US006998247B2

(12) United States Patent  (10) Patent No.: US 6,998,247 B2
Monfre et al.  (45) Date of Patent: Feb. 14, 2006

(54) METHOD AND APPARATUS USING ALTERNATIVE SITE GLUCOSE DETERMINATIONS TO CALIBRATE AND MAINTAIN NONINVASIVE AND IMPLANTABLE ANALYZERS

(75) Inventors: Stephen L. Monfre, Gilbert, AZ (US); Kevin H. Hazen, Gilbert, AZ (US); Timothy L. Ruchti, Gilbert, AZ (US); Thomas B. Blank, Chandler, AZ (US); James R. Henderson, Phoenix, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 83 days.

(21) Appl. No.: 10/377,916

(22) Filed: Feb. 28, 2003

(65) Prior Publication Data

US 2004/0024553 A1    Feb. 5, 2004

Related U.S. Application Data

(60) Provisional application No. 60/362,899, filed on Mar. 8, 2002, provisional application No. 60/362,885, filed on Mar. 8, 2002.

(51) Int. Cl.
    *C12Q 1/54*    (2006.01)
(52) U.S. Cl. ...................................... 435/14
(58) Field of Classification Search ............... 435/14; 250/339.09, 339.11, 252.1, 341.5; 356/39
    See application file for complete search history.

(56) References Cited

U.S. PATENT DOCUMENTS

| 6,240,306 | B1 | 5/2001 | Rohrscheib et al. |
| 6,280,381 | B1 * | 8/2001 | Malin et al. ............... 600/322 |
| 6,309,884 | B1 * | 10/2001 | Cooper et al. ............... 436/14 |
| 6,487,429 | B1 * | 11/2002 | Hockersmith et al. ...... 600/316 |
| 6,512,936 | B1 | 1/2003 | Monfre et al. ........... 600/322.1 |
| 6,528,809 | B1 * | 3/2003 | Thomas et al. ............. 250/573 |
| 6,615,061 | B1 * | 9/2003 | Khalil et al. ............... 600/310 |
| 6,654,620 | B1 * | 11/2003 | Wu et al. ................... 600/310 |
| 6,675,030 | B1 * | 1/2004 | Ciurczak et al. ............ 600/316 |
| 2001/0016682 | A1 * | 8/2001 | Berner et al. ............... 600/345 |
| 2002/0019022 | A1 * | 2/2002 | Dunn et al. .................. 435/14 |

FOREIGN PATENT DOCUMENTS

WO    WO/16905 A2    2/2002

OTHER PUBLICATIONS

Blank T. B. Clinical Results from a Noninvasive Blood Glucose Monitor. Proceedings of SPIE vol. 4624. 1-10, May 23, 2002.*
Tamada J. Nonivasive Glucose Monitoring. JAMA 282(19 (1839-1844, Nov. 17, 1999.*
U.S. Appl. No. 09/766,427, pending, Hockersmith et al.
Diabetes Statistics. Bethesda, MD: National Institute of Health, Publication No. 98-3926, Nov. 1997.
The Diabetes Control and Complications Trial Research Group. The effect of intensive treatment of diabetes on the development and progression of long-term complications in insulin-dependent diabetes mellitus. N Eng J of Med 1993: 329:977-86.
U.K. Prospective Diabetes Study (UKPDS) Group, "Intensive blood-glucose control with sulphonylureas or insulin compared with conventional treatment and risk of complications in patients with type 2 diabetes," Lancet, vol. 352, pp. 837-853, 1998.
Ohkubo, Y., H. Kishikawa, E. Araki, T. Miyata, S. Isami, S. Motoyoshi, Y. Kojima, N. Furuyoshi, and M. Shichizi, "Intensive insulin therapy prevents the progression of diabetic microvascular complications in Japanese patients with non-insulin-dependent diabetes...," Diabetes Res Clin Pract, vol. 28, pp. 103-117, 1995.
Hazen, Kevin H. "Glucose Determination in Biological Matrices Using Near-Infrared Spectroscopy", doctoral dissertation, University of Iowa, 1995.
Trajanowski, Zlatko; Brunner, Gemot A.; Schaupp, Lucas; Ellmerer, Martin; Wach, Paul; Pieber, Thomas R.; Kotanko, Peter; Skrabai, Falko "Open-Flow Microperfusion of Subcutaneous Adipose Tissue for ON-Line Continuous Ex Vivo Measurement of Glucose Concentration", Diabetes Care, 20, 1997, 1114-1120.
Trajanowski, Zlatko; Wach, Paul; Gfrerer, Robert "Portable Device for Continuous Fractionated Blood Sampling and Continuous ex vivo Blood Glucose Monitoring", Biosensors and Bioelectronics, 11, 1996, 479-487.

(Continued)

*Primary Examiner*—Ralph Gitomer
(74) *Attorney, Agent, or Firm*—Michael A. Glenn; Glenn Patent Group

(57)    ABSTRACT

Methods for calibrating noninvasive or implantable glucose analyzers utilize either alternative invasive glucose determinations or noninvasive glucose determinations for calibrating noninvasive or implantable glucose analyzers. Use of an alternative invasive or noninvasive glucose determination in the calibration allows minimization of errors due to sampling methodology, and spatial and temporal variation that are built into the calibration model. An additional method uses statistical correlations between noninvasive and alternative invasive glucose determinations and traditional invasive glucose determinations to adjust noninvasive or alternative invasive glucose concentrations to traditional invasive glucose concentrations. The methods provide a means for calibrating on the basis of glucose determinations that reflect the matrix observed and the variable measured by the analyzer more closely. A glucose analyzer couples an invasive fingerstick meter to a noninvasive glucose analyzer for calibration, validation, adaptation, and safety check of the calibration model embodied in the noninvasive analyzer.

37 Claims, 17 Drawing Sheets

OTHER PUBLICATIONS

Szuts, Ete Z.; Lock, J. Paul; Malomo, Kenneth J.; Anagnostopoulos, Althea "Blood Glucose Concentrations of Arm and Finger During Dynamic Glucose Conditions", Diabetes Technology & Therapeutics, 4, 2002, 3-11.

Lee, Debra M.; Weinert, Sandra E.; Miller, Earl E. "A Study of Forearm Versus Finger Stick Glucose Monitoring", Diabetes Technology & Therapeutics, 4, 2002, 13-23.

Bennion, Nancy; Christensen, Nedra K.; McGarraugh, Geoff "Alternate Site Glucose Testing: A Crossover Design", Diabetes Technology & Therapeutics, 4, 2002, 25-33.

Peled, Nina; Wong, Daniel; Gwalani, Shilpa "Comparison of Glucose Levels in Capillary Blood Samples from a Variety of Body Sites", Diabetes Technology & Therapeutics, 4, 2002, 35-44.

Jungheim, Karsten; Koschinsky, Theodor "Glucose Monitoring at the Arm", Diabetes Care, 25, 2002, 956-960.

Jungheim, Karsten; Koschinsky, Theodor "Risky Delay of Hypoglycemia Detection by Glucose Monitoring at the Arm", Diabetes Care, 24, 2001, 1303-1304.

McGarraugh, Geoff "Response to Jungheim and Koschinsky", Diabetes Care, 24, 2001, 1304-1306.

McGarraugh, Geoff; Schwartz, Sherwyn; Weinstein, Richard "Glucose Measurements Using Blood Extracted from the Forearm and the Finger", TheraSense, Inc., ART01022 Rev. C, 2001.

McGarraugh, Geoff; Price, David; Schwartz, Sherwyn; Weinstein, Richard "Physiological Influences on Off-Finger Glucose Testing", Diabetes Technology & Therapeutics, 3, 2001, 367-376.

Ryan, T.J. "A Study of the Epidermal Capillary Unit in Psoriasis", Dermatologica, 1969, 138, 459-472.

Fisher, Jerome S.; Hazen, Kevin H.; Welch, Matthew; Hockersmith, Linda; Coates, Jennifer "Comparisons of Capillary Blood Glucose Concentrations from the Fingertips amd Volar Aspects...", American Diabetes Association, 62nd Annual Meeting, Jun. 14, 2002 .

Welch, Matt; Hazen, Kevin "Alternative Site: Fingertop vs. Forearm", Instrumentation Metrics, Inc. Internal Report, Dec. 12, 2001.

Harvey, V: Sparks, skin and muscle. In: Johnson PC, ed. Peripheral Circulation. New York, 1978, 198.

Fisher, Jerome S.; Hazen, Kevin H.; Welch, Matthew; Hockersmith, Linda; Guttridge, Ryan J.; Ruchti, Timothy L. "Physiological Differences Between Volar and Dorsal Capillary Foreman Glucose...", American Diabetes Association, 62nd Annual Mtg., Jun. 14, 2002.

Khalil OS. "Spectroscopic and clinical aspects of non-invasive glucose measurements," Clin Chem 1999;45:165-77.

Zheng, P, C.E. Kramer, C.W. Barnes, J.R. Braig, B.B. Sterling, "Noninvasive Glucose Determination by Oscillating Thermal Gradient Spectrometry," Diabetes Technology & Therapeutics, vol. 2, No. 1, pp. 17-25.

Klonoff, D. C., "Noninvasive Blood Glucose Monitoring," Diabetes Care, vol. 20, No. 3, pp. 433-437, Mar. 1997.

Johnson, Paul C., Ph.D.; *Peripheral Circulation*, A Wiley Medical Publication; 1978.

Malin. S. et al "Noninvasive Prediction of Glucose by Near Infrared Spectroscopy", Clinical Chemistry, 1999, vol. 45, No. 9, pp. 1651-1658.

Blank, T. et al., "Clinical Results from a Noninvasive Blood Glucose Monitor", Optical Diagnostics and Sensing of Biological Fluids and Glucose and Cholesterol Monitoring II. 2002 Proceedings of SPIE vol. 4624. pp. 1-10.

Jungheim, K., et al. Risky Delay of Hypoglycemia Detection by Glucose Monitoring at the Arm. Diabetes Care. vol. 24, No. 7. Jul. 2001.

Junghiem K., et al. Glucose Monitoring at the Arm. Diabetes Card., vol. 25, No. 6. Jun. 2002.

* cited by examiner

METHOD AND APPARATUS USING ALTERNATIVE SITE GLUCOSE DETERMINATIONS TO CALIBRATE AND MAINTAIN NONINVASIVE AND IMPLANTABLE ANALYZERS

CROSS REFERENCE TO RELATED APPLICATION

This application claims benefit of U.S. Provisional Patent Application Ser. No. 60/362,899, filed Mar. 8, 2002 and U.S. Provisional Patent Application Ser. No. 60/362,885, filed Mar. 8, 2002.

BACKGROUND OF THE INVENTION

1. Field of the Invention

The invention relates generally to the calibration and maintenance of glucose analyzers. More particularly, the invention relates to the use of alternative site glucose determinations to improve algorithm development, calibration, and/or quality control of noninvasive or implantable glucose analyzers.

2. Background Information

Diabetes is a chronic disease that results in improper production and utilization of insulin, a hormone that facilitates glucose uptake into cells. While a precise cause of diabetes is unknown, genetic factors, environmental factors, and obesity appear to play roles. Diabetics have increased risk in three broad categories: cardiovascular heart disease, retinopathy, and neuropathy. Diabetics may have one or more of the following complications: heart disease and stroke, high blood pressure, kidney disease, neuropathy (nerve disease and amputations), retinopathy, diabetic ketoacidosis, skin conditions, gum disease, impotence, and fetal complications. Diabetes is a leading cause of death and disability worldwide. Moreover, diabetes is merely one among a group of disorders of glucose metabolism that also includes impaired glucose tolerance, and hyperinsulinemia, or hypoglycemia.

Diabetes Prevalence and Trends

Diabetes is an ever more common disease. The World Health Organization (WHO) estimates that diabetes currently afflicts 154 million people worldwide. There are 54 million people with diabetes living in developed countries. The WHO estimates that the number of people with diabetes will grow to 300 million by the year 2025. In the United States, 15.7 million people or 5.9 percent of the population are estimated to have diabetes. Within the United States, the prevalence of adults diagnosed with diabetes increased by six percent in 1999 and rose by 33 percent between 1990 and 1998. This corresponds to approximately eight hundred thousand new cases every year in America. The estimated total cost to the United States economy alone exceeds $90 billion per year. *Diabetes Statistics,* National Institutes of Health, Publication No. 98-3926, Bethesda, Md. (November 1997).

Long-term clinical studies show that the onset of complications can be significantly reduced through proper control of blood glucose levels. The Diabetes Control and Complications Trial Research Group, *The effect of intensive treatment of diabetes on the development and progression of long-term complications in insulin-dependent diabetes mellitus,* N Eng J of Med, 329:977–86 (1993); U.K. Prospective Diabetes Study (UKPDS) Group, *Intensive blood-glucose control with sulphonylureas or insulin compared with conventional treatment and risk of complications in patients with type 2 diabetes,* Lancet, 352:837–853 (1998); and Y. Ohkubo, H. Kishikawa, E. Araki, T. Miyata, S. Isami, S. Motoyoshi, Y. Kojima, N. Furuyoshi, M. Shichizi, *Intensive insulin therapy prevents the progression of diabetic microvascular complications in Japanese patients with non-insulin-dependent diabetes mellitus: a randomized prospective 6-year study,* Diabetes Res Clin Pract, 28:103–117 (1995).

A vital element of diabetes management is the self-monitoring of blood glucose levels by diabetics in the home environment. However, current monitoring techniques discourage regular use due to the inconvenient and painful nature of drawing blood through the skin prior to analysis. The Diabetes Control and Complication Trial Research Group, supra. As a result, noninvasive measurement of glucose has been identified as a beneficial development for the management of diabetes. Implantable glucose analyzers eventually coupled to an insulin delivery system providing an artificial pancreas are also being pursued.

Glucose Measurement History, Approaches, and Technologies

Diabetes treatment has progressed through several stages. The combined development of insulin therapy and in-home glucose determination led to a radical improvement in the lives of diabetics. Home glucose determination has also progressed through its own succession of stages. Urine tests for glucose have given way to the invasive fingerstick glucose determinations that are more accurate but somewhat painful, also presenting a possible biohazard. The development of alternative site glucose determinations has somewhat mitigated the pain aspects, but may have introduced a new difficulty as a result of temporal and spatial differences in glucose between the well perfused fingertip and the less well perfused alternative sites. Additionally, the biohazard issue remains. Current research is focusing on the development of noninvasive technologies that will totally eliminate the pain associated with glucose determination and fluid biohazard issues. Finally, considerable progress has been made in implantable or full-loop systems incorporating both glucose determination and insulin delivery that will result in the realization of an artificial pancreas. Blood glucose determination may currently be categorized into four major types:
  traditional invasive;
  alternative invasive;
  noninvasive; and
  implantable.

Due to the wide use of these modes of measurement and somewhat loose utilization of terminology in the literature, a detailed summary of the terminology for each mode of measurement is provided here in order to clarify usage of the terms herein.

In the medical field, the term 'invasive' is customarily applied to surgical methods and procedures, generally involving at least some trauma or injury to the tissue, such as cutting, in order to achieve their object. However, in the glucose determination field, the term 'invasive' is defined relative to noninvasive. 'Noninvasive' clearly describes methods, invariably signal-based, in which no biological sample or fluid is taken from the body in order to perform a glucose measurement. 'Invasive' then means that a biological sample is collected from the body. Invasive glucose determinations may then be further broken into two separate groups. The first is a 'traditional invasive' method in which a blood sample is collected from the body from an artery, vein, or capillary bed in the fingertips or toes. The second is an 'alternative invasive' method in which a sample of blood, interstitial fluid, or biological fluid is drawn from a region other than an artery, vein, or capillary bed in the fingertips or toes.

1. Traditional Invasive Glucose Determination

There are three major categories of traditional (classic) invasive glucose determinations. The first two utilize blood drawn with a needle from an artery or vein, respectively. The third consists of capillary blood obtained via lancet from the fingertip or toes. Over the past two decades, this has become the most common method for self-monitoring of blood glucose.

Common technologies are utilized to analyze the blood collected by venous or arterial draw and finger stick approaches. Glucose analysis includes techniques such as colorimetric and enzymatic glucose analysis. The most common enzymatic based glucose analyzers utilize glucose oxidase, which catalyzes the reaction of glucose with oxygen to form gluconolactone and hydrogen peroxide as shown by equation 1, infra. Glucose determination includes techniques based upon depletion of oxygen in the sample either through the changes in sample pH, or through the formation of hydrogen peroxide. A number of colorimetric and electro-enzymatic techniques further utilize the reaction products as a starting reagent. For example, hydrogen peroxide reacts in the presence of platinum to form the hydrogen ion, oxygen, and current; any of which may be utilized indirectly to determine the glucose concentration, as in equation 2.

$$\text{glucose} + O_2 \rightarrow \text{gluconolactone} + H_2O_2 \quad (1)$$

$$H_2O_2 \rightarrow 2H^+ + O_2 + 2e^- \quad (2)$$

It is noted that a number of alternative site methodologies such as the THERASENSE FREESTYLE (THERASENSE, INC., Alameda Calif.) collect blood samples from regions other than the fingertip or toes. These technologies are not herein referred to as traditional invasive glucose meters unless the sample is drawn from the fingertip or toes despite having similar chemical analyses such as the calorimetric or enzymatic analysis described above. However, the same device utilized to collect blood via lancet from sample sites consisting of the fingertip or toe is a traditional invasive glucose analyzer.

2. Alternative Invasive Glucose Determination

There are several alternative invasive methods of determining glucose concentration. A first group of alternative invasive glucose analyzers have a number of similarities to the traditional invasive glucose analyzers. One similarity is that blood samples are acquired with a lancet. Obviously, this form of alternative invasive glucose determination while unsuitable for analysis of venous or arterial blood, may be utilized to collect capillary blood samples. A second similarity is that the blood sample is analyzed using chemical analyses that resemble the colorimetric and enzymatic analyses describe above. The primary difference, however, is that in an alternative invasive glucose determination the blood sample is not collected from the fingertip or toes. For example, according to package labeling, the THERASENSE FREESTYLE meter may be utilized to collect and analyze blood from the forearm. This is an alternative invasive glucose determination due to the location of the lancet draw. In this first group of alternative invasive methods based upon blood draws with a lancet, a primary difference between the alternative invasive and traditional invasive glucose determination is the location of the site of blood acquisition from the body. Additional differences include factors such as the gauge of the lancet, the depth of penetration of the lancet, timing issues, the volume of blood acquired, and environmental factors such as the partial pressure of oxygen, altitude, and temperature. This form of alternative invasive glucose determination includes samples collected from the palmar region, base of thumb, forearm, upper arm, head, earlobe, torso, abdominal region, thigh, calf, and plantar region.

A second group of alternative invasive glucose analyzers is distinguished by their mode of sample acquisition. This group of glucose analyzers has a common characteristic of acquiring a biological sample from the body or modifying the surface of the skin to gather a sample without utilization of a lancet for subsequent analysis. For example, a laser poration based glucose analyzer utilizes a burst or stream of photons to create a small hole in the skin surface. A sample of substantially interstitial fluid collects in the resulting hole. Subsequent analysis of the sample for glucose constitutes an alternative invasive glucose analysis, whether or not the sample was actually removed from the created hole. A second common characteristic is that a device and algorithm are utilized to determine glucose from the sample. Herein, the term alternative invasive includes techniques that analyze biosamples such as interstitial fluid, whole blood, mixtures of interstitial fluid and whole blood, and selectively sampled interstitial fluid. An example of selectively sampled interstitial fluid is collected fluid in which large or less mobile constituents are not fully represented in the resulting sample. For this second group of alternative invasive glucose analyzers sampling sites include: the hand, fingertips, palmar region, base of thumb, forearm, upper arm, head, earlobe, eye, chest, torso, abdominal region, thigh, calf, foot, plantar region, and toes. A number of methodologies exist for the collection of samples for alternative invasive measurements including:

Laser poration: In these systems, photons of one or more wavelengths are applied to skin creating a small hole in the skin barrier. This allows small volumes of interstitial fluid to become available for a number of sampling techniques;

Applied current: In these systems, a small electrical current is applied to the skin allowing interstitial fluid to permeate through the skin;

Suction: In these systems, a partial vacuum is applied to a local area on the surface of the skin. Interstitial fluid permeates the skin and is collected.

In all of the above techniques, the analyzed sample is interstitial fluid. However, some of these same techniques can be applied to the skin in a fashion that draws blood. For example, the laser poration method can result in blood droplets. As described herein, any technique that draws biosamples from the skin without the use of a lancet on the fingertip or toes is referred to as an alternative invasive technique. In addition, it is recognized that the alternative invasive systems each use different sampling approaches that lead to different subsets of the interstitial fluid being collected. For example, large proteins might lag behind in the skin while smaller, more diffusive, elements may be preferentially sampled. This leads to samples being collected with varying analyte and interferent concentrations. Another example is that a mixture of whole blood and interstitial fluid may be collected. These techniques may be utilized in combination. For example the SOFT-TACT, also known as the SOFTSENSE (ABBOT LABORATORIES, INC. Abbot Park Ill.), applies suction to the skin followed by a lancet stick. Despite the differences in sampling, these techniques are referred to as alternative invasive techniques sampling interstitial fluid.

The literature occasionally refers to the alternative invasive technique as an alternative site glucose determination or as a minimally invasive technique. The minimally invasive nomenclature derives from the method by which the sample is collected. As described herein, the alternative site glucose determinations that draw blood or interstitial fluid, even microliter, are considered to be alternative invasive glucose determination techniques as defined above. Examples of alternative invasive techniques include the THERASENSE FREESTYLE when not sampling fingertips or toes, the GLUCOWATCH (CYGNUS, INC., Redwood City Calif.) the ONE TOUCH ULTRA (LIFESCAN, INC., Milpitas Calif.), and equivalent technologies.

A wide range of technologies serve to analyze biosamples collected with alternative invasive techniques. The most common of these technologies are:

Conventional: With some modification, the interstitial fluid samples may be analyzed by most of the technologies utilized to determine glucose concentrations in serum, plasma, or whole blood. These include electrochemical, electroenzymatic, and colorimetric approaches. For example, the enzymatic and colorimetric approaches described above may also be used to determine the glucose concentration in interstitial fluid samples;

Spectrophotometric: A number of approaches for determining the glucose concentration in biosamples, have been developed that utilize spectrophotometric technologies. These techniques include: Raman and fluorescence, as well as techniques using light from the ultraviolet through the infrared [ultraviolet (200 to 400 nm), visible (400 to 700 nm), near-IR (700 to 2500 nm or 14,286 to 4000 $cm^{-1}$), and infrared (2500 to 14,285 nm or 4000 to 700 $cm^{-1}$)].

As used herein, the term invasive glucose analyzer encompasses both traditional invasive glucose analyzers and alternative invasive glucose analyzers.

3. Noninvasive Glucose Determination

There exist a number of noninvasive approaches for glucose determination. These approaches vary widely, but have at least two common steps. First, an apparatus is utilized to acquire a signal from the body without obtaining a biological sample. Second, an algorithm is utilized to convert this signal into a glucose determination.

One type of noninvasive glucose determination is based upon spectra. Typically, a noninvasive apparatus utilizes some form of spectroscopy to acquire the signal or spectrum from the body. Utilized spectroscopic techniques include, but are not limited to: Raman and fluorescence, as well as techniques using light from ultraviolet through the infrared [ultraviolet (200 to 400 nm), visible (400 to 700 nm), near-IR (700 to 2500 nm or 14,286 to 4000 $cm^{-1}$), and infrared (2500 to 14,285 nm or 4000 to 700 $cm^{-1}$)]. A particular range for noninvasive glucose determination in diffuse reflectance mode is about 1100 to 2500 nm or ranges therein. K. Hazen, *Glucose Determination in Biological Matrices Using Near-Infrared Spectroscopy*, doctoral dissertation, University of Iowa (1995). It is important to note that these techniques are distinct from the traditional invasive and alternative invasive techniques listed above in that the sample interrogated is a portion of the human body in-situ, not a biological sample acquired from the human body.

Typically, three modes are utilized to collect noninvasive scans: transmittance, transflectance, and/or diffuse reflectance. For example the signal collected, typically consisting of light or a spectrum, may be transmitting through a region of the body such as a fingertip, diffusely reflected, or transflected. Transflected here refers to collection of the signal not at the incident point or area (diffuse reflectance), and not at the opposite side of the sample (transmittance), but rather at some point on the body between the transmitted and diffuse reflectance collection area. For example, transflected light enters the fingertip or forearm in one region and exits in another region typically 0.2 to 5 mm or more away depending on the wavelength utilized. Thus, light that is strongly absorbed by the body such as light near water absorbance maxima at 1450 or 1950 nm would need to be collected after a small radial divergence and light that is less absorbed such as light near water absorbance minima at 1300, 1600, or 2250 nm may be collected at greater radial or transflected distances from the incident photons.

Noninvasive techniques are not limited to using the fingertip as a measurement site. Alternative sites for taking noninvasive measurements include: a hand, finger, palmar region, base of thumb, forearm, volar aspect of the forearm, dorsal aspect of the forearm, upper arm, head, earlobe, eye, tongue, chest, torso, abdominal region, thigh, calf, foot, plantar region, and toe. It is important to note that noninvasive techniques do not have to be based upon spectroscopy. For example, a bioimpedence meter would be considered a noninvasive device. Within the context of the invention, any device that reads a signal from the body without penetrating the skin and collecting a biological sample is referred to as a noninvasive glucose analyzer. For example, a bioimpedence meter is a noninvasive device.

An alternative reference method is a reference determination made at a location on the body not including the fingertips and toes. An alternative reference includes both an alternative invasive measurement and an alternative site noninvasive measurement. Hence, an alternative site noninvasive measurement is a noninvasive measurement made at physiological sites excluding the fingertips and toes.

4. Implantable Sensor for Glucose Determination

There exist a number of approaches for implanting a glucose sensor into the body for glucose determination. These implantables may be utilized to collect a sample for further analysis or may acquire a reading or signal from the sample directly or indirectly. Two categories of implantable glucose analyzers exist: short-term and long-term.

As referred to herein, a device or a collection apparatus is at least a short-term implantable (as opposed to a long-term implantable) if part of the device penetrates the skin for a period of greater than 3 hours and less than one month. For example, a wick placed subcutaneously to collect a sample overnight that is removed and analyzed for glucose content representative of the interstitial fluid glucose concentration is referred to as a short term implantable. Similarly, a biosensor or electrode placed under the skin for a period of greater than three hours that reads a signal indicative of a glucose concentration or level, directly or indirectly is referred to as at least a short-term implantable device. Conversely, devices described above based upon techniques like a lancet, applied current, laser poration, or suction are referred to as either a traditional invasive or alternative invasive technique as they do not fulfill both the three hour and skin penetration parameters. As described herein, long-term implantables are distinguished from short-term implantables by having the criteria that they must both penetrate the skin and be utilized for a period of one month or longer. Long term implantables may remain in the body for many years.

Implantable glucose analyzers vary widely, but have at least several features in common. First, at least part of the device penetrates the skin. More commonly, the entire device is imbedded into the body. Second, the apparatus is utilized to acquire either a sample of the body or a signal relating directly or indirectly to the glucose concentration within the body. If the implantable device collects a sample, readings or measurements on the sample may be collected after removal from the body. Alternatively, readings or signals may be transmitted from within the body by the device or utilized for such purposes as insulin delivery while in the body. Third, an algorithm is utilized to convert the signals into readings directly or indirectly related to the glucose concentration. An implantable analyzer may read signals from one or more of a variety of body fluids or tissues including but not limited to: arterial blood, venous blood, capillary blood, interstitial fluid, and selectively sampled interstitial fluid. An implantable analyzer may also collect glucose information from skin tissue, cerebral spinal fluid, organ tissue, or through an artery or vein. For example, an implantable glucose analyzer may be placed transcutaneously, in the peritoneal cavity, in an artery, in muscle, or in an organ such as the liver or brain. The implantable glucose sensor may be one component of an artificial pancreas.

Examples of implantable glucose monitors follow. One example of a CGMS (continuous glucose monitoring system) is a group of glucose monitors based upon open-flow microperfusion. Z. Trajanowski, G. Brunner, L. Schaupp, M. Ellmerer, P. Wach, T. Pieber, P. Kotanko, F. Skrabai, *Open-flow microperfusion of subcutaneous adipose tissue for on-line continuous ex vivo measurement of glucose concentration,* Diabetes Care, 20:1114–1120 (1997). Another example utilizes implanted sensors that comprise biosensors and amperometric sensors. Z. Trajanowski, P. Wach, R. Gfrerer, *Portable device for continuous fractionated blood sampling and continuous ex vivo blood glucose monitoring,* Biosensors and Bioelectronics, 11:479–487 (1996). Another example is the MINIMED CGMS (MEDTRONIC, INC., Minneapolis Minn.).

DESCRIPTION OF RELATED TECHNOLOGY

Glucose Concentration Measured at Fingertip vs. Alternative Sampling Locations Many authors claim that alternative site glucose concentrations are equivalent to fingerstick glucose determination. A number of examples are summarized below:

Szuts, et al. conclude that measurable physiological differences in glucose concentration between the arm and fingertip could be determined, but that these differences were found to be clinically insignificant even in those subjects in whom they were measured. E. Szuts, J. Lock, K. Malomo, A. Anagnostopoulos, Althea, *Blood glucose concentrations of arm and finger during dynamic glucose conditions,* Diabetes Technology & Therapeutics, 4:3–11 (2002).

Lee, et al. concluded that patients testing two hours postprandial could expect to see small differences between their forearm and fingertip glucose concentrations. D. Lee, S. Weinert, E. Miller, *A study of forearm versus finger stick glucose monitoring,* Diabetes Technology & Therapeutics, 4:13–23 (2002).

Bennion, et al. concluded that there is no significant difference in $HbA_1C$ measurements for patients utilizing alternative site meters off of the fingertip and traditional glucose analyzers on the fingertip. N. Bennion, N. Christensen, G. McGarraugh, *Alternate site glucose testing: a crossover design,* Diabetes Technology & Therapeutics, 4:25–33 (2002). This is an indirect indication that the forearm and fingertip glucose concentrations are the same, though many additional factors such as pain and frequency of testing will impact the study.

Peled, et al. concluded that glucose monitoring of blood samples from the forearm is suitable when expecting steady state glycemic conditions and that the palm samples produced a close correlation with fingertip glucose determinations under all glycemic states. N. Peled, D. Wong, S. Gwalani, *Comparison of glucose levels in capillary blood samples from a variety of body sites,* Diabetes Technology & Therapeutics, 4:35–44 (2002).

Based upon a study utilizing fast acting insulin injected intravenously, Jungheim, et al. suggested that to avoid risky delays in hyperglycemia and hypoglycemia detection, monitoring at the arm should be limited to situations in which ongoing rapid changes in the blood glucose concentration can be excluded. K. Jungheim, T. Koschinsky, *Glucose monitoring at the arm,* Diabetes Care, 25:956–960 (2002); and K. Jungheim; T. Koschinsky, *Risky delay of hypoglycemia detection by glucose monitoring at the arm,* Diabetes Care, 24:1303–1304 (2001). The use of intravenous insulin in this study was criticized as creating physiological extremes that influence the observed differences. G. McGarraugh, *Response to Jungheim and Koschinsky,* Diabetes Care, 24:1304:1306 (2001).

Equilibration Approaches

While there exist multiple reports that glucose concentrations are very similar when collected from the fingertip or alternative locations, a number of sampling approaches have been recommended to increase localized perfusion at the sample site to equilibrate the values just prior to sampling. Several of these approaches are summarized below:

Pressure: One sampling methodology requires rubbing or applying pressure to the sampling site in order to increase localized perfusion prior to obtaining a sample via lancet. An example of this is the FREESTYLE blood glucose analyzer (THERASENSE, INC., supra). G. McGarraugh, S. Schwartz, R. Weinstein, *Glucose Measurements Using Blood Extracted from the Forearm and the Finger,* THERASENSE, INC., ART01022 Rev. C (2001); and G. McGarraugh, D. Price, S. Schwartz, R. Weinstein, *Physiological influences on off-finger glucose testing,* Diabetes Technology & Therapeutics, 3:367–376 (2001).

Heating: Heat applied to the localized sample site has been proposed as a mechanism for equalizing the concentration between the vascular system and skin tissue. This may be to dilate the capillaries allowing more blood flow, which leads towards equalization of the venous and capillary glucose concentrations. Alternatively, vasodilating agents such as nicotinic acid, methyl nicotinamide, minoxidil, nitroglycerin, histamine, capsaicin, or menthol can be utilized to increase local blood flow. M. Rohrscheib, C. Gardner, M. Robinson, *Method and apparatus for noninvasive blood analyte measurement with fluid compartment equilibration,* U.S. Pat. No. 6,240,306 (May 29, 2001).

Vacuum: Applying a partial vacuum to the skin at and around the sampling site prior to sample collection has also been utilized. A localized deformation in the skin may allow superficial capillaries to fill more completely. T. Ryan, *A*

*study of the epidermal capillary unit in psoriasis,* Dermatologica, 138:459–472 (1969). For example, ABBOT LABORATORIES, INC. utilizes a vacuum device at one-half atmosphere that pulls the skin up 3.5 mm into their device. ABBOT maintains this deformation results in increased perfusion that equalizes the glucose concentration between the alternative site and the fingertip. R. Ng, Presentation to the FDA at the Clinical Chemistry & Clinical Toxicology Devices Panel Meeting, Gaithersburg Md. (Oct. 29, 2001).

Calibration:

Glucose analyzers require calibration. This is true for all types of glucose analyzers such as traditional invasive, alternative invasive, noninvasive, and implantable analyzers. One fact associated with noninvasive glucose analyzers is the fact that they are secondary in nature, that is, they do not measure blood glucose levels directly. This means that a primary method is required to calibrate these devices to measure blood glucose levels properly. Many methods of calibration exist.

Calibration of Traditional Invasive Glucose Analyzers:

Glucose meters or analyzers may be calibrated off of biological samples such as whole blood, serum, plasmas, or modified solutions of these samples. In addition, glucose analyzers may be calibrated with a range of whole blood samples, modified whole blood samples, blood simulants, phantoms, or a range of chemically prepared standards. Typically, these samples have glucose concentrations that span the desired functionality range of the glucose analyzer. For glucose analyzers, this is approximately 70 to 400 mg/dL. Some go further into the hypoglycemic range, down to 40 or even 0 mg/dL, while some go well into the hyperglycemic range, up to 700 or 1000 mg/dL.

Calibration of Alternative Invasive Glucose Analyzers:

Alternative invasive glucose analyzers utilize many of the invasive glucose calibration procedures. When calibrating the alternative invasive glucose meters that utilize biological fluids such as blood or interstitial fluid as a reference, relatively minor modifications to the traditional calibration approaches may be required.

Calibration of Noninvasive Glucose Analyzers:

One noninvasive technology, near-infrared spectroscopy, provides the opportunity for both frequent and painless noninvasive measurement of glucose. This approach involves the illumination of a spot on the body with near-infrared (NIR) electromagnetic radiation, light in the wavelength range 700 to 2500 nm. The light is partially absorbed and scattered, according to its interaction with the constituents of the tissue. The actual tissue volume that is sampled is the portion of irradiated tissue from which light is transflected or diffusely transmitted to the spectrometer detection system. With near-infrared spectroscopy, a mathematical relationship between an in vivo near-infrared measurement and the actual blood glucose value needs to be developed. This is achieved through the collection of in vivo NIR measurements with corresponding blood glucose values that have been obtained directly through the use of measurement tools like the HEMOCUE (YSI INCORPORATED, Yellow Springs Ohio), or any appropriate and accurate traditional invasive reference device.

For spectrophotometric based analyzers, there are several univariate and multivariate methods that can be used to develop the mathematical relationship between the measured signal and the actual blood glucose value. However, the basic equation being solved is known as the Beer-Lambert Law. This law states that the strength of an absorbance/reflectance measurement is proportional to the concentration of the analyte which is being measured, as in equation 3, $$A = \epsilon b C \qquad (3)$$

where A is the absorbance/reflectance measurement at a given wavelength of light, $\epsilon$ is the molar absorptivity associated with the molecule of interest at the same given wavelength, b is the distance that the light travels, and C is the concentration of the molecule of interest (glucose).

Chemometric calibration techniques extract the glucose signal from the measured spectrum through various methods of signal processing and calibration including one or more mathematical models. The models are still developed through the process of calibration on the basis of an exemplary set of spectral measurements known as the calibration set and associated set of reference blood glucose values based upon an analysis of fingertip capillary blood or venous blood. Common multivariate approaches requiring an exemplary reference glucose concentration vector for each sample spectrum in a calibration include partial least squares (PLS) and principal component regression (PCR). Many additional forms of calibration are known, such as neural networks.

Because every method has error, it is desirable that the primary device used to measure blood glucose be as accurate as possible to minimize the error that propagates through the mathematical relationship developed. While it appears reasonable to assume that any FDA-approved blood glucose monitor should be suitable, for accurate verification of the secondary method, a monitor having a percentage error of less than 5 percent is desirable. Meters with increased percentage error such as 10 percent may also be acceptable, though the error of the device being calibrated may increase.

Although the above is well-understood, one aspect that is forgotten is that secondary methods require constant verification that they are providing consistent and accurate measurements when compared to the primary method. This means that a method for checking blood glucose values directly and comparing those values with the given secondary method is required. Such monitoring is manifested in quality assurance and quality control programs. Bias adjustments are often made to a calibration. In some cases the most appropriate calibration is selected based upon these secondary methods. S. Malin, T. Ruchti, *Intelligent system for noninvasive blood analyte prediction,* U.S. Pat. No. 6,280, 381 (Aug. 28, 2001). This approach is also known as validation.

The Problem:

Calibration of a noninvasive glucose analyzer entails some complications not observed in traditional invasive glucose analyzers. For example, spectroscopic or spectrophotometric based noninvasive glucose analyzers probe a sample that is not entirely whole blood or interstitial fluid. Photons penetrate into the body, interact with body layers and/or tissues and are detected upon reemerging from the body. Hence, many possible interferences exist that do not exist in a prepared reference or calibration sample. In addition, the interferences and matrices encountered are part of a living being and hence are dynamic in nature. For these reasons, indirect calibration is often attempted with traditional invasive reference glucose determinations collected from the fingertip. This approach, however, introduces errors into the noninvasive analyzer that are associated with sampling the reference glucose concentration. One key source of error is the difference between glucose concentrations at the site tested by the noninvasive glucose analyzer and the reference site sampled with an invasive technology. Thus, it would be an important advance in the art to provide methods for calibrating and maintaining signal-based analyzers that addressed the negative effect on their accuracy and precision that results from calibrating them based on invasive reference samples taken at sites distant from the site of noninvasive sampling.

SUMMARY OF THE INVENTION

The invention provides methods for utilizing either alternative invasive glucose determinations or alternative site noninvasive glucose determinations for calibrating noninvasive or implantable glucose analyzers. Use of an alternative invasive or alternative site noninvasive glucose determination in the calibration allows for minimization of errors built into the glucose analyzer model, including errors due to sampling, methodology, and error due to temporal and spatial variation of glucose concentration within the subject's body. In addition, the method provides conversion of glucose concentrations determined from noninvasive or alternative reference determinations into traditional invasive glucose determinations. As described herein, the use of an alternative invasive or noninvasive glucose determination for calibration is also understood to include their utilization for glucose determination, prediction, calibration transfer, calibration maintenance, quality control, and quality assurance.

The use of alternative invasive or alternative site noninvasive reference determinations provides a means for calibrating on the basis of glucose determinations that reflect the matrix observed and the variable measured by the analyzer more closely. Statistical correlations between noninvasive and alternative invasive glucose determinations and traditional invasive glucose determinations may then be utilized to adjust alternative site noninvasive or alternative invasive glucose concentrations to traditional invasive glucose concentrations. The invention also provides an apparatus in which a invasive stick meter is coupled to a noninvasive glucose analyzer for calibration, validation, adaptation, and safety check of the calibration model embodied in the noninvasive analyzer.

DETAILED DESCRIPTION

The present invention reduces the error in the reference glucose concentration for the calibration of glucose sensors and therefore leads to a more accurate, precise, and robust glucose measurement system.

Difference in Traditional Invasive and Alternative Invasive Glucose Concentration Initially, differences between traditional invasive and alternative invasive glucose determinations are demonstrated. It is demonstrated here that the differences between the alternative invasive glucose concentration from a site such as the forearm and the glucose concentration from a traditional invasive fingerstick vary as a function of at least time and location. Additional parameters include sampling methodology, physiology, and glucose analyzer instrumentation.

EXAMPLE #1

In a first example, variation of glucose concentration at locations in the body is demonstrated at fixed points in time. A total of twenty diabetic subjects were run through one of two glucose profiles each having two peaks so that the resulting curves formed the shape of an 'M,' shown in part in FIG. 1, over a period of eight hours. Thus, glucose concentration started low at around 80 mg/dL, was increased to approximately 350 mg/dL, and was brought back to about 80 mg/dL in a period of about four hours. The cycle was immediately repeated to form an 'M'-shaped glucose concentration profile. These profiles were alternately generated with intake of a liquid form of carbohydrate (50–100 g) or intake of a solid form of carbohydrate (50–100 g) in combination with insulin to generate the two excursions of the 'M' profile. Traditional invasive fingertip capillary glucose concentrations were determined every 15 minutes throughout the 8-hour period. Each fingertip determination was immediately followed by an alternative invasive capillary glucose determinations wherein samples were collected from the volar aspect of the subject's right and then left forearms. The resulting data set included 1920 data points (20 subjects*3 sites/15 minutes*32 draws/day). J. Fischer, K. Hazen, M. Welch, L. Hockersmith, J. Coates, *Comparisons of capillary blood glucose concentrations from the fingertips and the volar aspects of the left and right forearms,* American Diabetes Association, $62^{nd}$ Annual Meeting, (Jun. 14, 2002). The 'M'-shaped profiles described above may be induced according to procedures previously set forth in L. Hockersmith, A method of producing a glycemic profile of predetermined shape in a test subject, U.S. patent application Ser. No. 09/766,427 (Jan. 18, 2001), the entirety of which is hereby incorporated by reference as if fully set forth herein.

Figure 1:
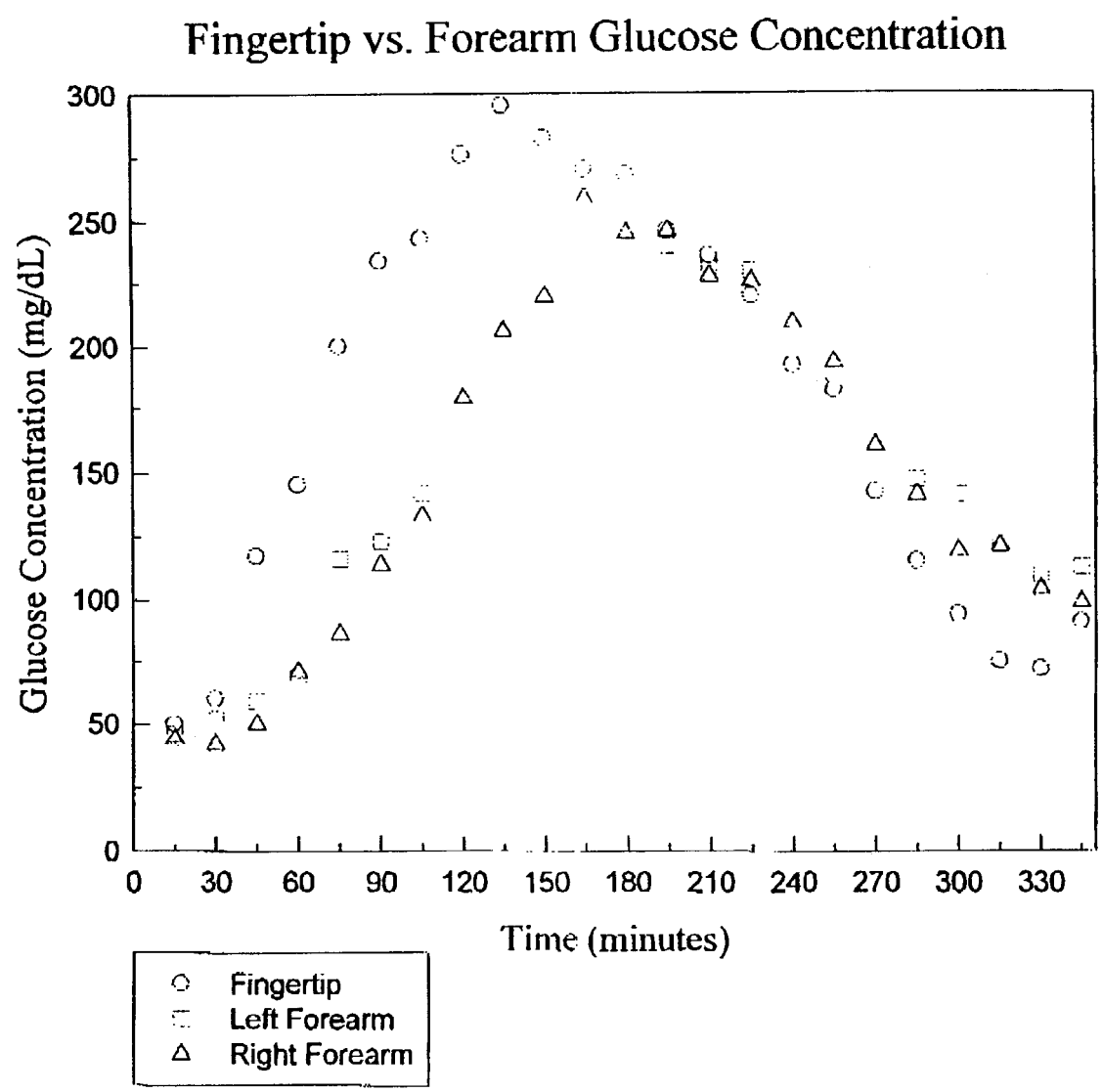
FIG. 1 provides a plot of glucose measurements that demonstrates large differences in glucose concentration between the fingertip and forearm according to the invention.
Figure 2:
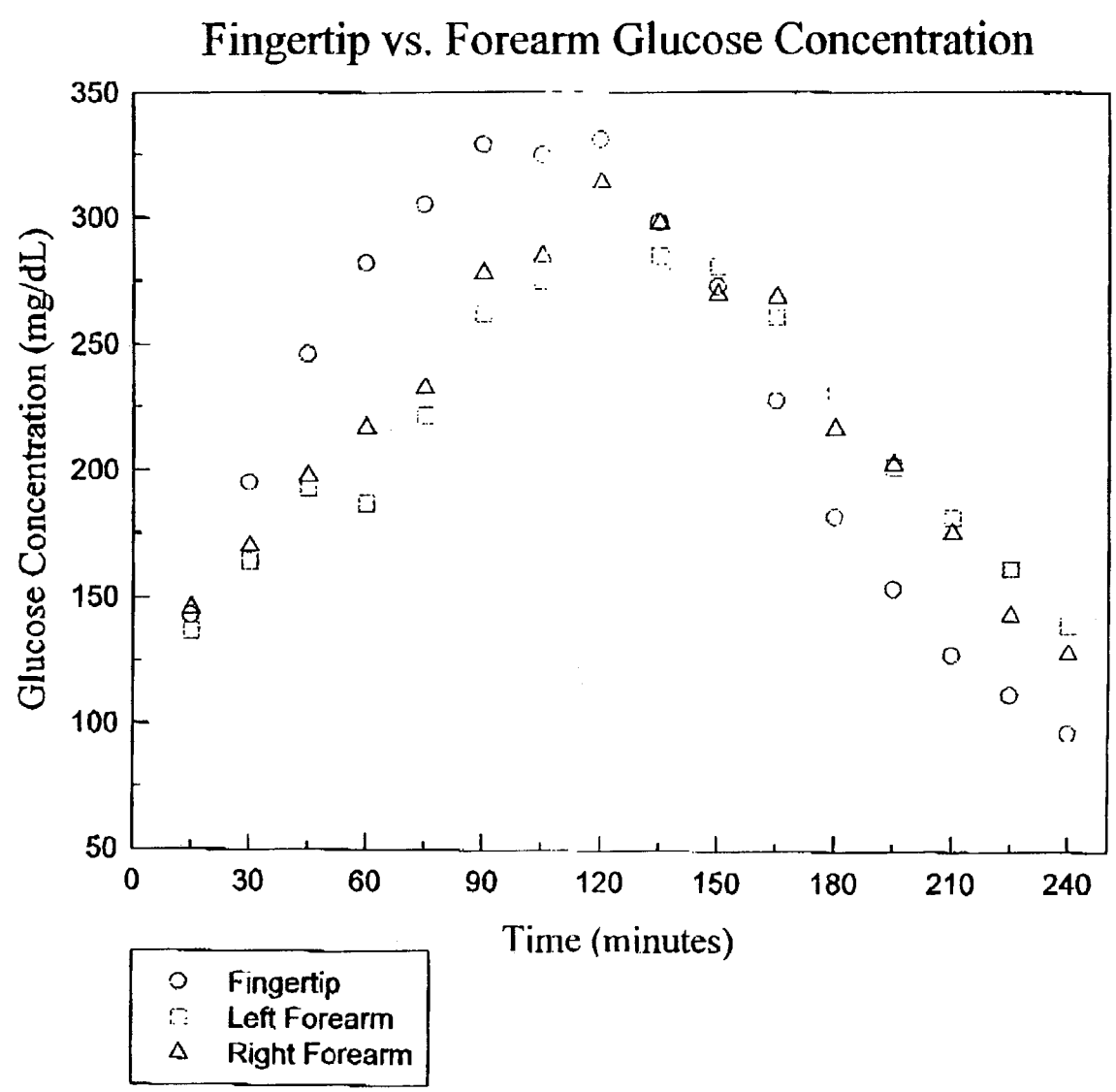
FIG. 2 provides a plot of glucose measurements that demonstrates a lag in glucose concentrations determined from the forearm compared to the fingertip according to the invention.
Figure 3:
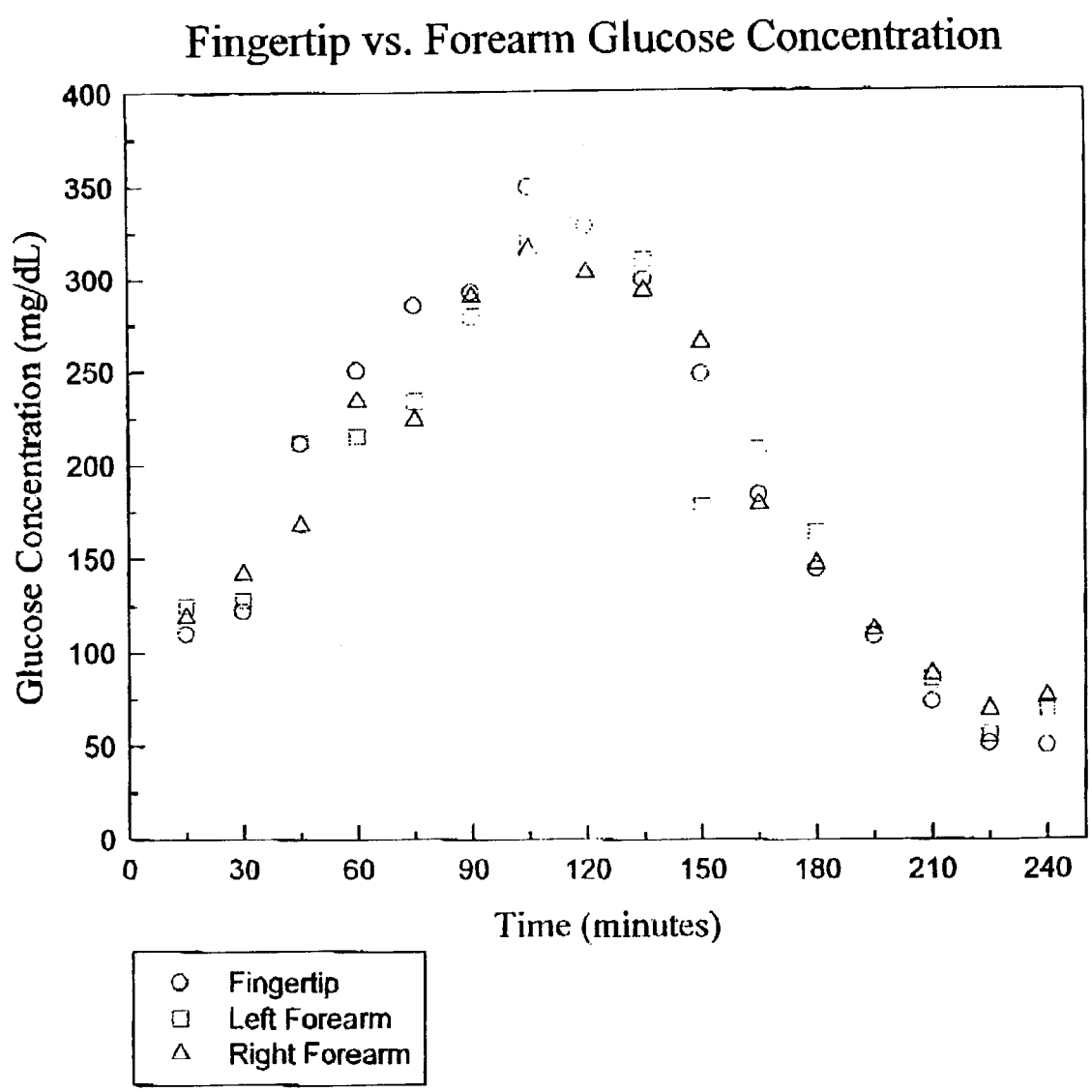
FIG. 3 shows a plot of fingertip and forearm glucose concentrations that are well correlated.
Figure 4:
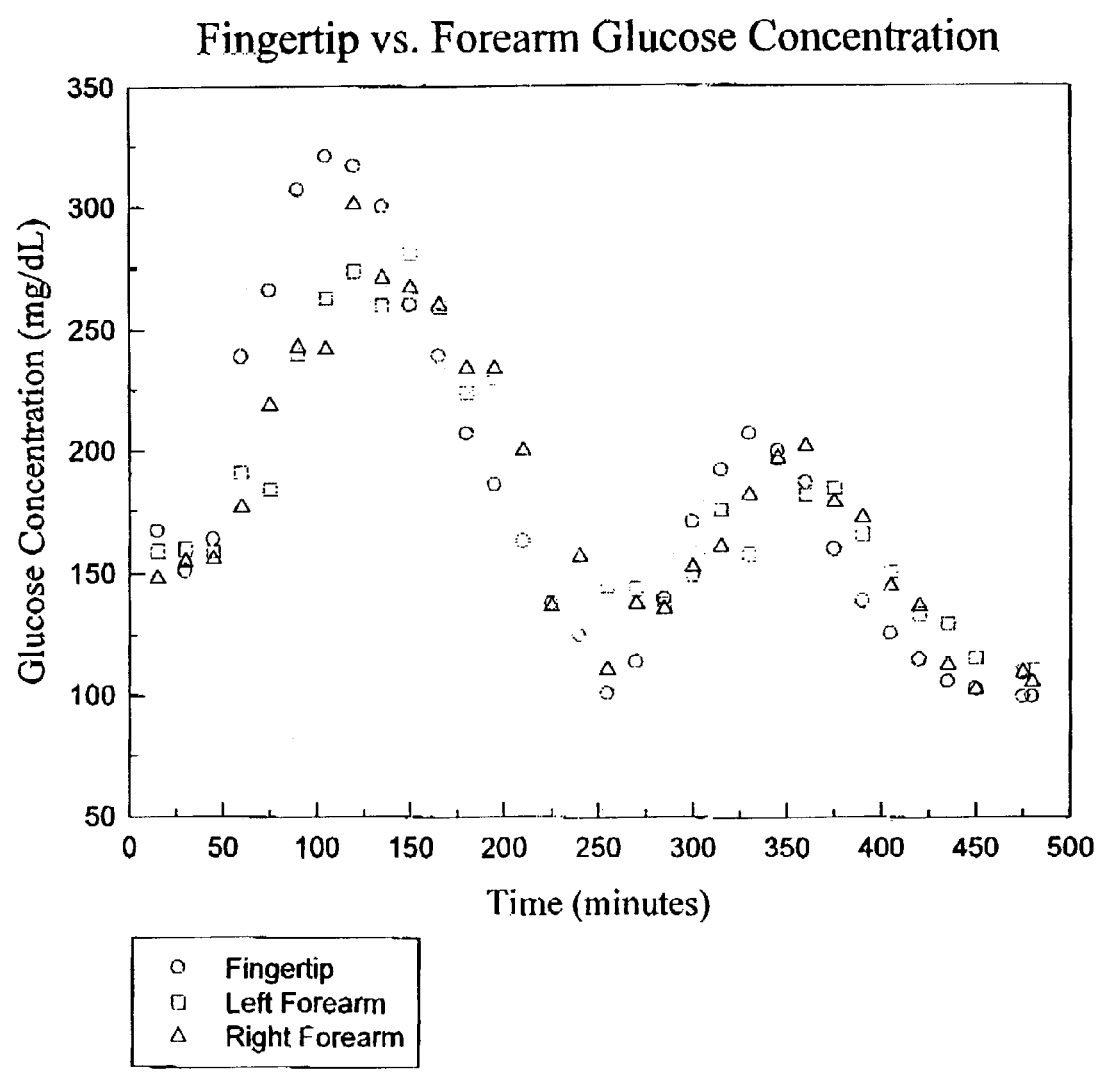
FIG. 4 illustrates a plot that demonstrates historesis in glucose concentration profiles resulting in differences in glucose concentration between the fingertip and forearm even when glucose concentrations are at a local minimum with respect to time according to the invention.

Four partial 'M' profiles from the above study are presented here. In FIG. 1, alternative invasive glucose concentrations measured at the forearm are demonstrated to have both a dampened and a lagged profile versus the traditional invasive fingertip glucose concentrations. For this individual, when the glucose concentration was rising the forearm glucose concentrations are observed to be substantially dampened, that is lower than the corresponding fingertip glucose concentration. For example, at the 90 minute mark the fingertip glucose concentration of 234 mg/dL is more than 100 mg/dL higher than either the left or right forearm glucose concentration of 123 and 114 mg/dL, respectively. In addition, the peak glucose concentration observed at the fingertip of 295 mg/dL is both larger and occurred 30 minutes earlier than the peak forearm glucose concentration of 259 mg/dL. Finally, the forearm glucose concentrations have a small lag versus the fingertip glucose concentrations. FIG. 2 presents another glucose profile in which many of the same effects just described are observed but to a lesser degree. For example, the rising glucose concentrations of the alternative invasive forearm glucose concentrations are still less than those of the traditional invasive fingertip glucose concentrations, but the difference is smaller. A dampening and lag of the alternative invasive peak are still observed. One measure of dampening is the range of traditional invasive glucose concentrations minus the range of alternative invasive glucose concentrations. In addition, the lag is more pronounced than in the previous figure. FIG. 3 demonstrates another example in which the forearm glucose concentrations closely track those of the fingertip glucose concentrations. Finally, FIG. 4 demonstrates a historesis effect as a subject moves through subsequent glucose excursions. That is, a lag observed in a forearm may still be observed at a later time. In this case, dampening of the forearm glucose concentration is observed at a glucose minimum relative to that of the fingertip glucose concentration. The effects observed above are representative as a whole of the glucose profiles observed in the study outlined above.

Figure 5:
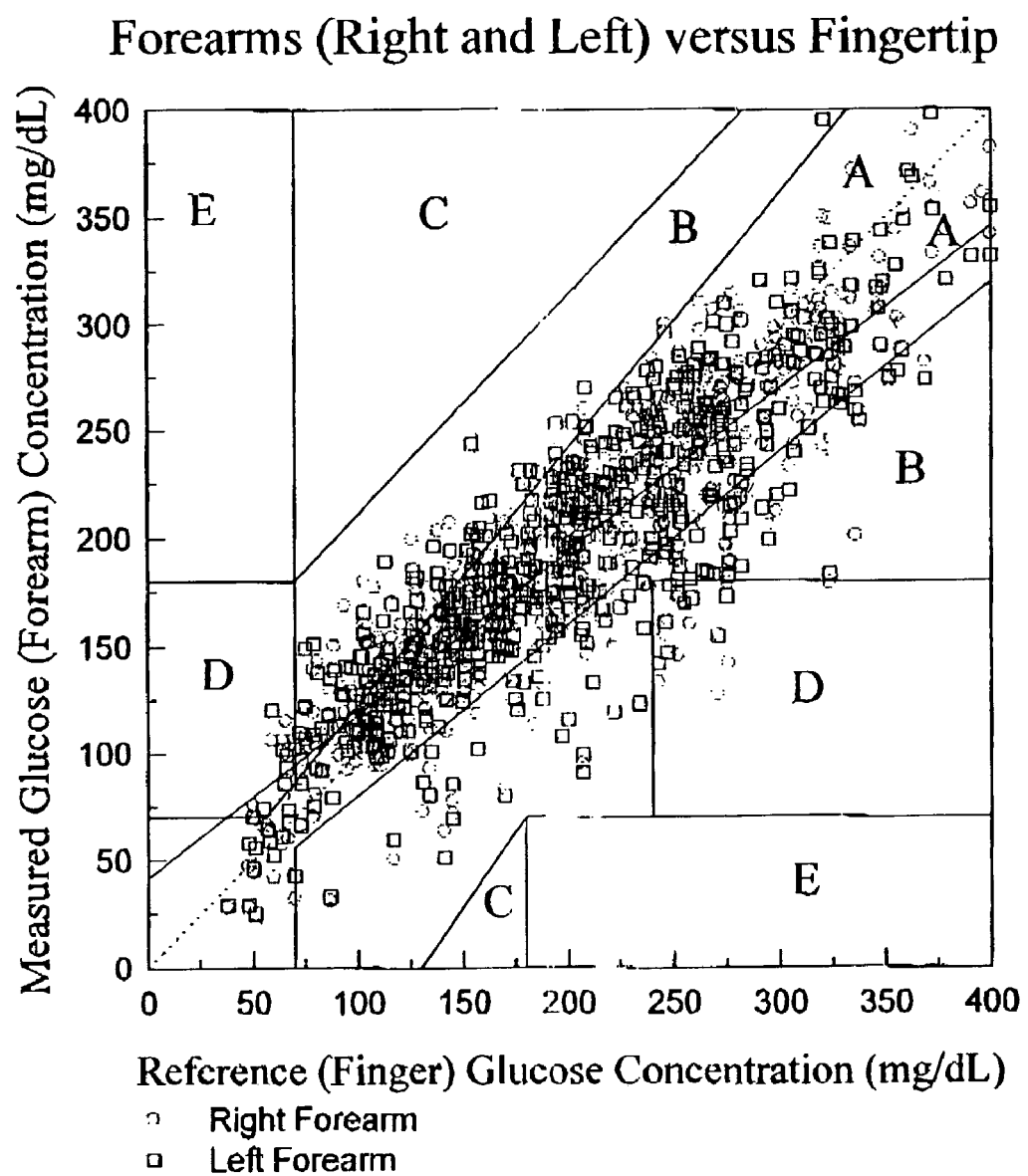
FIG. 5 provides a plot of forearm glucose concentrations against corresponding fingertip glucose concentrations with a relatively large error according to the invention.

As in FIG. 5, alternative invasive glucose determinations collected from the volar aspect of each subject's left and right forearm are plotted against the time-associated traditional invasive fingertip reference glucose concentration for all subjects in a concentration correlation plot overlaid with a Clarke error grid. The standard error of the forearm glucose concentrations versus the fingertip glucose concentration is relatively large at 37.7 mg/dL with an F-value of 4.43. The best fit of the data yields a slope of 0.76 and an intercept of 41.4 mg/dL. This is consistent with dampened and delayed forearm glucose profiles relative to the fingertip and results in only 73.8% of the points falling in the 'A' region of the Clarke error grid.

Figure 6:
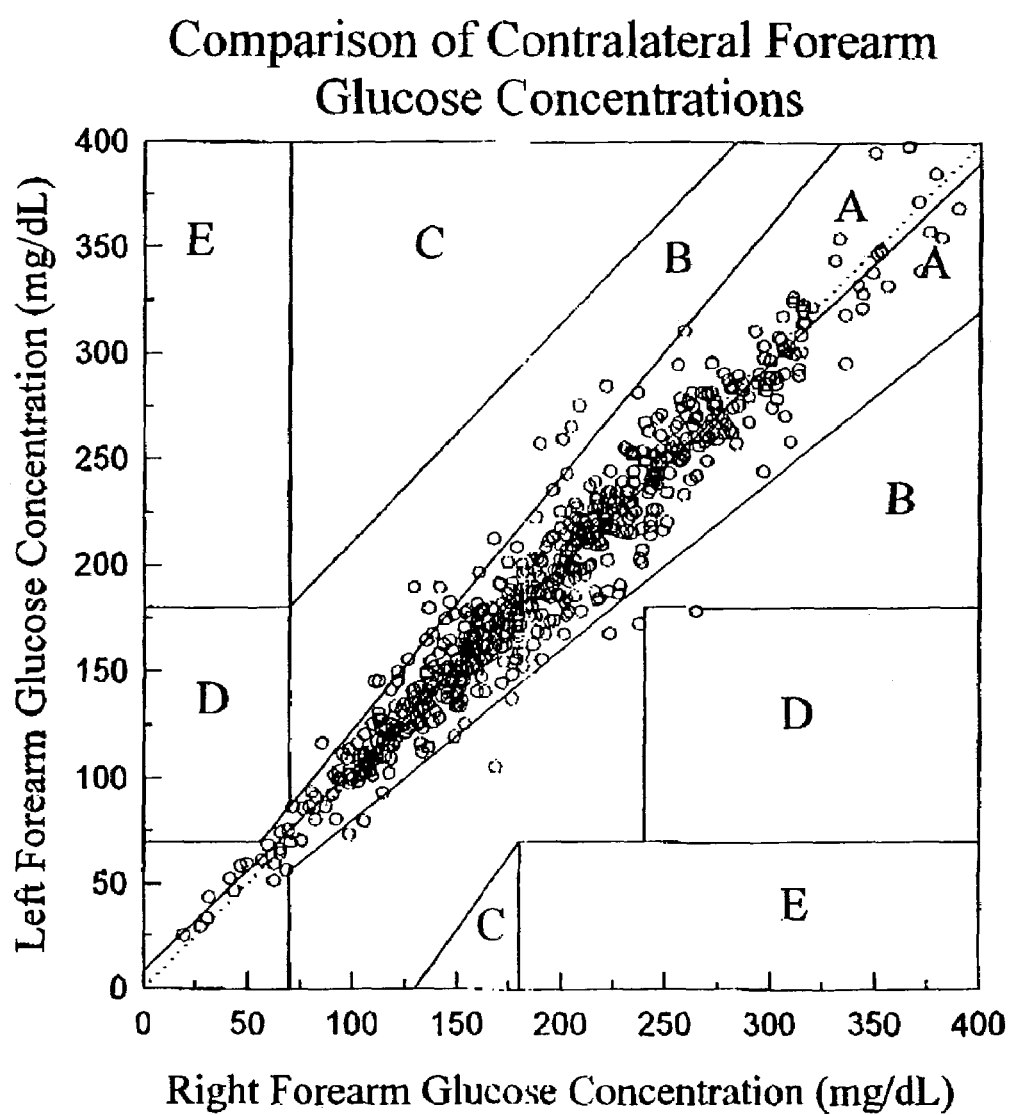
FIG. 6 provides a plot of forearm glucose concentrations against corresponding contralateral forearm glucose concentrations with a smaller error when compared to FIG. 5, according to the invention.

The glucose determinations collected from the volar aspect of each subject's left and right forearm are plotted against each other for all subjects on a Clarke error grid in FIG. 6. The standard error of the left forearm glucose concentrations versus the right forearm glucose concentration is reduced to 17.2 mg/dL with an F-value of 16.0. The best fit of the data yields a slope of 0.96 and an intercept of 8.3 mg/dL. This is consistent with a reduction in the dampening and delay of left forearm glucose profiles relative to the right forearm glucose concentrations and results in 95.8 percent of the points falling in the 'A' region of the Clarke error grid. A slope of 0.96, combined with the low standard error, indicates that the capillary blood glucose values of the left and right volar forearm would be similar.

These data suggest several conclusions:
during a glucose excursion, substantial differences are often observed between the capillary blood glucose of the untreated forearm and the fingertip;
fast changes in blood glucose concentration magnify differences between the measured blood glucose concentration of the fingertip and forearm while the relative errors are proportional to the glucose concentration;
during periods of rapid change in blood glucose concentration, differences between the forearm and fingertip give rise to a higher percentage of points in less desirable regions of the Clarke error grid;
the measured blood glucose concentrations of the volar aspect of the left and right forearms appear similar; and
finally, these findings are consistent with the phenomenon of decreased perfusion into the forearm versus that of the fingertip, leading to a dampening and/or lag in the glucose profile.

These conclusions are consistent with those reported in the circulatory physiology literature and that relating to sampling approaches of alternative invasive glucose analyzers. It has been reported that blood flow in the fingers is 33±10 mL/g/min at 20° C. while in the leg, forearm, and abdomen the blood flow is 4–6 mL/g/min at 19–22° C. V. Harvey, Sparks, *skin and muscle,* in: *Peripheral Circulation,* P. Johnson, ed., p.198, New York (1978). This is consistent with the observed differences in localized blood glucose concentration. When glucose concentrations vary rapidly a difference develops throughout the body in local blood glucose concentrations as a result of differences in local tissue perfusion. For example, the blood flow in the fingers of the hand is greater than in alternative sites. This means that the blood glucose in the fingertips will equilibrate more rapidly with venous blood glucose concentrations. Furthermore, the magnitude of differences in local glucose concentrations between two sites is related to the rate of change in blood glucose concentrations. Conversely, under steady-state glucose conditions, the glucose concentration throughout the body tends to be uniform.

An additional study demonstrated that localized variations in the glucose concentration in the dorsal versus volar aspect of the forearm are small versus differences between the glucose concentrations observed in either forearm region versus that of the fingertip. J. Fischer, K. Hazen, M. Welch, L. Hockersmith, R Guttridge, T. Ruchti, *physiological differences between volar and dorsal capillary forearm glucose concentrations and finger stick glucose concentrations in diabetics,* American Diabetes Association, 62$^{nd}$ Annual Meeting (Jun. 14, 2002).

Another study demonstrated very small localized variation in glucose concentration within a region such as the dorsal aspect of the forearm with observed differences approximating the scale of the error observed in the reference method. The glucose concentrations in the forearm are not observed to vary within three inches laterally or axially from a central point of the forearm.

In addition to differences in perfusion, the local permeability of tissue to diffusion and the local uptake of glucose during exercise or other activity can cause non-uniform distribution of glucose in the body. Finally, when the noninvasive variable and the reference glucose concentration are not measured simultaneously, an additional error can occur when glucose is varying in the body.

Physiology

The following physiological interpretations are deduced from these studies:
- during times of glucose change, the glucose concentration as measured on the arm can lag behind that of the fingertip;
- a well-recognized difference between the fingertip and the forearm is the rate of blood flow;
- differences in circulatory physiology of the off-finger test sites may lead to differences in the measured blood glucose concentration;
- on average, the arm and finger glucose concentrations are approximately the same, but the correlation is not one-to-one. This suggests differences between traditional invasive glucose concentrations and alternative invasive glucose concentrations are different during time periods of fasting and after glucose ingestion;
- the relationship of forearm and thigh glucose levels to finger glucose is affected by proximity to a meal. Meter forearm and thigh results during the sixty and ninety minute postprandial testing sessions are consistently lower than the corresponding finger results;
- differences are inversely related to the direction of blood glucose concentration change;
- rapid changes may produce significant differences in blood glucose concentrations measured at the fingertip and forearm; and
- for individuals, the relationship between forearm and finger blood glucose may be consistent. However, the magnitude of the day-to-day differences has been found to vary. Finally, interstitial fluid (ISF) may lead plasma glucose concentration in the case of falling glucose levels due to exercise or glucose uptake due to insulin.

Utilization of the Difference in Traditional Invasive and Alternative Invasive Glucose Concentration The discrepancy between the glucose level at the noninvasive measurement site versus the reference concentration presents a fundamental issue in relation to calibration. A calibration is generally a mathematical model or curve that is used to convert the noninvasively measured variable such as absorbance, voltage, or intensity to an estimate of the glucose concentration. Determination of the calibration is performed on the basis of a set of paired data points composed of noninvasive variables and associated reference blood glucose concentrations collected through a blood draw. Any error introduced by the reference method is propagated into any error associated with the indirect method as an uncertain, imprecise, and/or biased calibration.

Method

The invention provides a method of developing a calibration based on either traditional or alternate invasive reference glucose measurements. The percentage error in the reference glucose concentration is reduced through the application of one or more techniques that improve correspondence between the reference glucose concentration and the glucose concentration reflected in the variable measured by the sensor, herein referred to as the "sensor variable", thus producing a superior exemplary set of calibration data for calculating the calibration curve or model. Both noninvasive and implantable glucose analyzers require a calibration because they rely on measurement of glucose indirectly from a blood or tissue property, fluid, parameter, or variable. While the target application is typically an optical sensor, any device that measures glucose through a calibration falls within the scope of the invention. Examples of such systems include:
- near-infrared spectroscopy (700–2500 nm), O. Khalil, *Spectroscopic and clinical aspects of non-invasive glucose measurements,"* Clin Chem, 45:165–77 (1999);
- far-infrared spectroscopy;
- mid-infrared spectroscopy;
- Raman spectroscopy;
- fluorescence spectroscopy;
- spectroscillating thermal gradient spectrometry, P. Zheng, C. Kramer, C. Barnes, J. Braig, B. Sterling, *Noninvasive glucose determination by oscillating thermal gradient spectrometry,* Diabetes Technology & Therapeutics, 2:1:17–25;
- impedance based glucose determination;
- nuclear magnetic resonance;
- optical rotation of polarized light;
- radio wave impedance;
- fluid extraction from the skin;
- glucose oxidase and enzymatic sensors;
- interstitial fluid harvesting techniques (e.g. microporation or application of a small electric current) or glucose electrode; and
- microdialysis.

As previously described, the calibration set constitutes a set of paired data points collected on one or more subjects; and generally includes glucose concentrations that span the expected range of glucose variation. Each paired data point includes a reference glucose value and an associated value or values of the sensor variable.

The invented method relies on a variety of processes that improve the reference values of the calibration set, which can be used independently or together.

First is a process for calibrating using a calibration set of paired data points including a reference glucose value from a traditional invasive method or an alternative invasive method and a noninvasive sensor measurement. This first process is based on the recognition that glucose tends to be uniform throughout the tissue under steady state conditions and that perfusion is the dominant physiological process leading to differences in glucose under dynamic situations. Within the context of this first process, a number of techniques are suggested for improving reference values with respect to their corresponding sensor values:

Paired data points are collected at intervals that allow determination of the rate of glucose change. For example, traditional invasive glucose determinations and noninvasive signals may be generated every 15 minutes for a period of four hours. The resulting calibration set is limited to paired data points with a corresponding rate of glucose change less than a specified maximum level.

Calibration data is collected during periods of stasis or slow change in glucose concentration. The rate of acceptable change in glucose concentration is determined on the basis of the tolerable error in the reference values. For example, a rate of change of 0.5 mg/dL/minute may be found to be acceptable;

Under dynamic conditions, the circulation at a measurement site is perturbed, both for an alternative invasive measurement site for calibration and later for measuring glucose utilizing an alternative invasive glucose analyzer. Enhancement of circulation in the forearm or alternate testing site, for example, causes the local glucose concentrations to approach those of the fingertip. As described above, methods for perturbing circulation may include ultrasound, or a variety of surface applications that cause vasodilatation, mechanical stimulation, partial vacuum, and heating;

Patients are screened according to the discrepancy between their traditional invasive glucose concentration at a fingertip or toe and an alternative invasive glucose determination at the alternative invasive site. For example, subjects with significant discrepancy between the glucose concentration in the fingertip and the local tissue volume sampled through a near-infrared device, such as a forearm, would not be used for calibration. Subjects having a small difference in glucose concentration between the traditional invasive and alternative invasive measurement site would be used for calibration. On this basis subjects are further screened for device applicability for subsequent glucose predictions; and Using post-processing techniques, the sensor's estimate of the glucose concentration is corrected. The method utilizes an estimate of the time lead or lag between the two glucose concentrations from a cross-correlation or time series analysis and a correction using an interpolation procedure. A similar correction would correct for a dampening of the noninvasive signal relative to a traditional invasive signal.

In a second process, careful site selection assures that reference values reflect the concentration of glucose in the sensor variable. According to this process, blood, serum, plasma, interstitial draws, or selective interstitial sample acquisitions are taken from a tissue site that is either near the sensor sample site or has been designed/determined to reflect the sample site. For example, when noninvasive (sensor) near-infrared measurements are taken for calibration on a forearm, it is possible in some individuals to collect a capillary blood draw from an alternative invasive sample site such as the same forearm or from the opposite forearm. The blood draws are taken in a manner that maintains perfusion equivalence to the noninvasive sample site.

It is noted that alternative invasive glucose determinations acquire samples from varying depths. Some acquire interstitial fluid from just below the epidermal later while others penetrate into capillary blood or subcutaneous fluids. Because a noninvasive glucose analyzer can be tuned to sense glucose concentrations from different depths, a logical choice of a reference device is an alternative invasive analyzer sampling from a similar depth in the skin. For example, a near-IR glucose analyzer functioning in the 2100 to 2300, 1550 to 1800, or 1100 to 1350 nm region acquires signal from approximately 1.5, 3, and 5 mm, respectively. Similarly, a glucose analyzer functioning within 50 nm of 1450, 1900 or 2500 nm samples at depths of less than 1 mm. Hence, noninvasive technologies that rely on tissue volumes primarily including the epidermis indirectly measure primarily interstitial glucose concentrations and may benefit from alternative invasive glucose analyzers sampling the interstitial fluid from the epidermis versus an alternative invasive glucose analyzer that samples blood from the dermis.

Finally, glucose varies dynamically through time in individuals. When a glucose determination through a blood or interstitial sample cannot be taken simultaneously with the sensor variable an error can exist due to the time differential. A technique for reducing this error is based on interpolation and extrapolation of the reference glucose values to the time the sensor variable was collected.

INSTRUMENTATION

Noninvasive

A number of technologies have been reported for measuring glucose noninvasively that involve the measurement of a tissue related variable. Examples include but are not limited to far-infrared absorbance spectroscopy, tissue impedance, Raman, and fluorescence, as well as techniques using light from the ultraviolet through the infrared [ultraviolet (200 to 400 nm), visible (400 to 700 nm), near-IR (700 to 2500 nm or 14,286 to 4000 $cm^{-1}$), and infrared (2500 to 14,285 nm or 4000 to 700 $cm^{-1}$)]. These techniques share the common characteristic that they are indirect measurements of glucose. A calibration is required in order to derive a glucose concentration from subsequent collected data. In the past, capillary finger blood glucose and venous blood glucose have been utilized to generate these calibrations. However, as has been shown, these traditional invasive glucose determinations do not always represent the glucose concentration at the sampled site.

A number of spectrometer configurations are possible for collecting noninvasive spectra of body regions. Typically, a spectrometer, also called a sensor, has one or more beam paths from a source to a detector. A light source may comprise a blackbody source, a tungsten-halogen source, one or more LED's, or one or more laser diodes. For multi-wavelength spectrometers a wavelength selection device may be utilized or a series of optical filters may be utilized for wavelength selection. Wavelength selection devices comprise dispersive elements such as one or more plane, concave, ruled, or holographic grating. Additional wavelength selective devices include an interferometer, successive illumination of the elements of an LED array, prisms, and wavelength selective filters. However, variation of the source such as varying which LED or diode is firing may be utilized. Detectors may in the form of one or more single element detectors or one or more arrays or bundles of detectors. Single element or array detectors maybe fabricated from InGaAs, PbS, PbSe, Si, MCT (mercury-cadmium-tellurium), or the like. Light collection optics such as fiber optics, lenses, and mirrors are commonly utilized in various configurations within a spectrometer to direct light from the source to the detector by way of a sample. The mode of operation may be transmission, diffuse reflectance, or transflectance. Due to changes in performance of the overall spectrometer, reference wavelength standards are often scanned. Typically, a wavelength standard is collected immediately before or after the interrogation of the tissue, but may also occur at times far removed such as when the spectrometer was originally manufactured. A typical reference wavelength standard would be polystyrene or a rare earth oxide such as holmium, erbium, or dysprosium oxide.

The interface of the glucose analyzer to the tissue includes a patient interface module and light such as near-infrared radiation is directed to and from the tissue either directly or through a light pipe, fiber-optics, a lens system, or a light directing mirror system. The area of the tissue surface to which near-infrared radiation is applied and the area of the tissue surface the returning near-infrared radiation is detected from are different and separated by a defined distance and their selection is designed to enable targeting of a tissue volume conducive to measurement of the property of interest. The patient interface module may include an elbow rest, a wrist rest, and/or a guide to assist in interfacing the illumination mechanism of choice and the tissue of interest. Generally, an optical coupling fluid is placed between the illumination mechanism and the tissue of interest to minimize specular reflectance from the surface of the skin.

Figure 7:
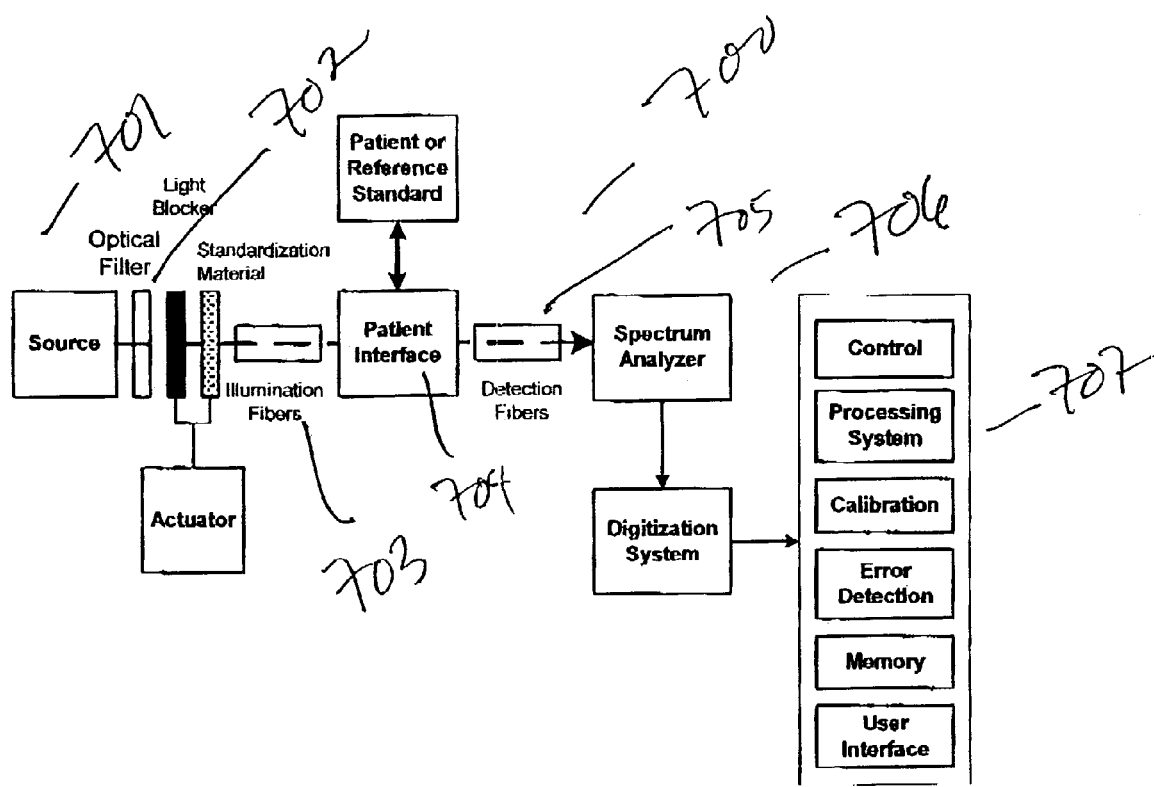
FIG. 7 shows a block diagram of a noninvasive analyzer using alternative site glucose determinations calibration and maintenance according to the invention.

A preferred embodiment of the sensor 700, shown in FIG. 7, is a spectroscopic measurement system that includes a tungsten halogen near-infrared radiation source, a wavelength selection filter 702 passing 1100 to 1900 nm light, fiber optics 703 for conveying the source photons to an in-vivo skin sample, an interface 704 to the forearm of a patient, fiber optic collection optics 705 for gathering diffusely reflected and transflected radiation from the skin to a grating, and an InGaAs array 706 to detect the radiation, electronic means 707 for converting the resulting signal into a glucose concentration and a display (not shown). D. Klonoff, *Noninvasive blood glucose monitoring,* Diabetes Care, 20:3:433 (March, 1997).

The sample site constitutes the point or area on the subject's body surface the measurement probe contacts and the specific tissue irradiated by the spectrometer system. Ideal qualities for a sample site include: 1) homogeneity, 2) immutability; and 3) accessibility to the target analyte. Noninvasive glucose analyzers commonly use the fingertip as a sampling site. However, several alternative sampling sites are possible, including the abdomen, upper arm, thigh, hand (palm or back of the hand) or ear lobe, in the preferred embodiment, the volar part of the forearm is used. In addition, while the measurement can be made in either diffuse reflectance or diffuse transmittance mode, the preferred method is diffuse reflectance. Scanning of the tissue can be done continuously when the tissue area being tested is not affected by pulsation effects, or the scanning can be done intermittently between pulses.

The collected signal (near-infrared radiation in this case) is converted to a voltage and sampled through an analog-to-digital converter for analysis on a microprocessor based system and the result displayed.

Implantable:

In an alternate arrangement, the system or a portion of the system is implanted, and the measurement is made directly on soft tissue, muscle, a blood vessel or skin tissue within the body. In this configuration, the measurement is made in a manner that is non-invasive to the probed tissue although the system or a portion of the system is implanted within the body. For example, the peritoneal cavity is a suitable location for implantation and both the probing signal source and detection system are implanted. In the preferred embodiment, telemetry is employed to transfer data or actual analyte readings to a remote location outside the body. Alternately, a transcutaneous connector is employed. After transfer, the data or concentration are then processed and displayed to the user or heath care provider. Three different embodiments of the implanted system are disclosed. The first, a consumer version, is used for incremental or continuous applications requiring intensive analysis of body analytes (e.g., glucose). A particularly useful application is nocturnal monitoring of glucose and detection or prediction of hypoglycemic events. In the second, the system is employed in a health care facility and the analyte is monitored via a computer or health care provider. A third embodiment of the implanted system is for use in a closed-loop insulin delivery system. In this embodiment the system is a sub-component of an artificial pancreas and used to monitor glucose levels for insulin dosage determination via an insulin pump.

In implantable embodiments, an alternative invasive or noninvasive reference glucose concentration or set of concentrations may be utilized with paired implantable signals in order to calibrate an implantable glucose analyzer. This is essentially the same as utilizing an alternative invasive glucose analyzer to calibrate a noninvasive glucose analyzer as discussed above. Utilization of an alternative invasive or noninvasive reference is beneficial in instances when the implantable glucose analyzer is sampling fluids or tissues that have perfusion similar to that of the alternative invasive sites. For example, a semi-implantable device may be placed into the subcutaneous tissue or an implantable device may be placed into the peritoneal cavity. Both of these regions may have dampened and lagged glucose concentrations that are similar to alternative invasive glucose determinations or noninvasive glucose determinations from regions that are not well perfused. Hence, the reference values will more closely represent the implantable signals. This will aid in calibration design and maintenance as above.

Correction of Alternative Invasive to Traditional Invasive Glucose Concentration In building a glucose calibration model, a number of measurement parameters must be considered. The selection of measurement parameters will greatly affect predicted glucose concentrations from subsequent spectra. For example, for glucose determination based on near-IR spectral measurements, parameters include sample selection, preprocessing step selection, and actual model parameters such as the number of factors in a multivariate model. In view of the demonstrated difference in glucose concentration between traditional and alternative measurements, selection of the appropriate set of glucose reference concentrations is also important.

For example, a model may be based on a calibration set that utilizes alternative invasive forearm glucose concentrations from the dorsal aspect of the forearm and near-IR noninvasive glucose determinations from the forearm. By using such a model to predict glucose concentrations from subsequent spectra, the subsequent measurements for a large number of subjects will correspond to the values of the calibration set more closely than if the calibration set were based on traditional invasive glucose determinations from a fingertip. The importance of parameter selection is described in greater detail below. Furthermore, a method for correcting measurements based on a calibration set of traditional invasive glucose determinations to approximate those based on a set of alternative invasive determinations is provided.

EXAMPLE

A single calibration model was applied to 4,980 noninvasive spectra collected from the volar aspect of the forearm of twenty-six subjects covering 233 unique visits utilizing nine instruments collected over a period of eight months. Each subject was tested every fifteen minutes for a period of approximately eight hours. The resulting glucose predictions were compared to both traditional invasive reference fingertip and alternative invasive reference forearm glucose concentrations.

Figure 8:
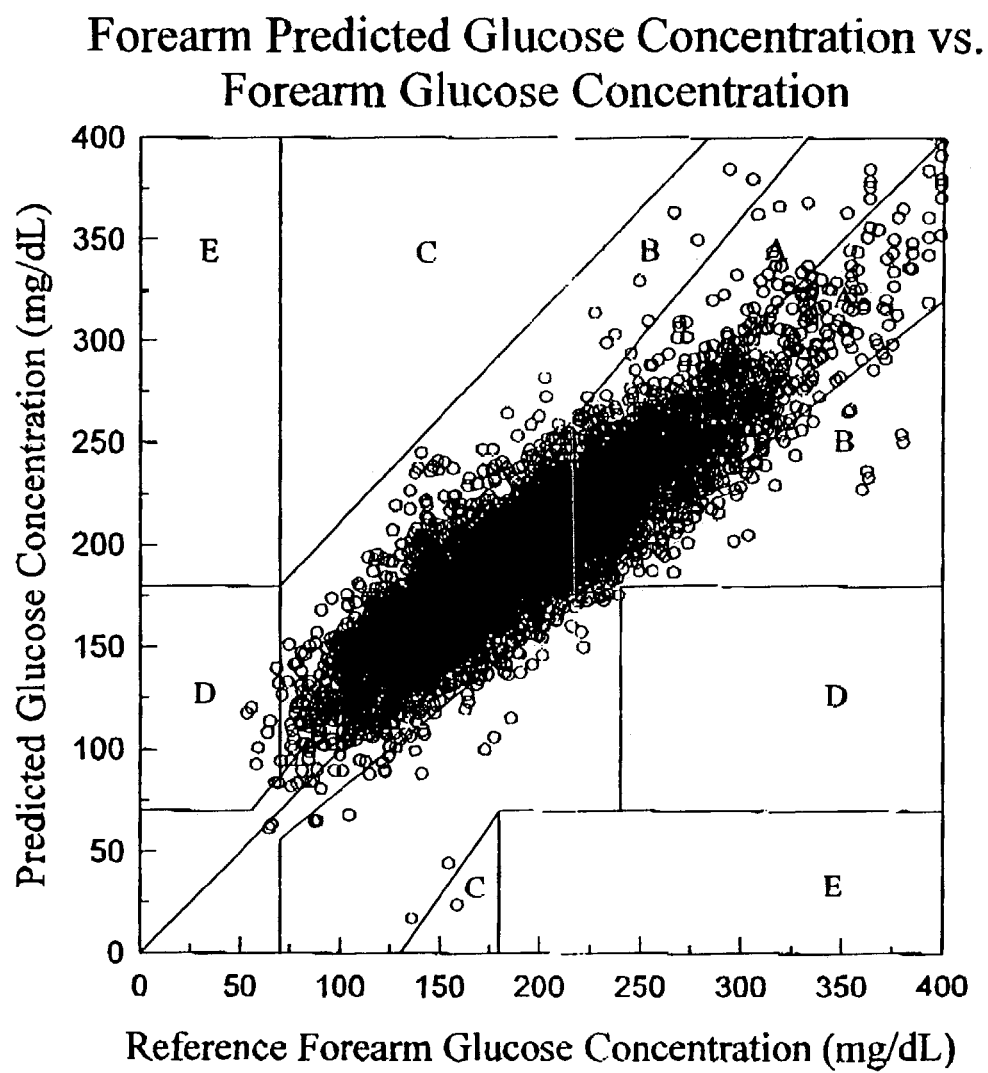
FIG. 8 shows a plot of predicted glucose concentrations versus reference forearm glucose determinations according to the invention.
Figure 9:
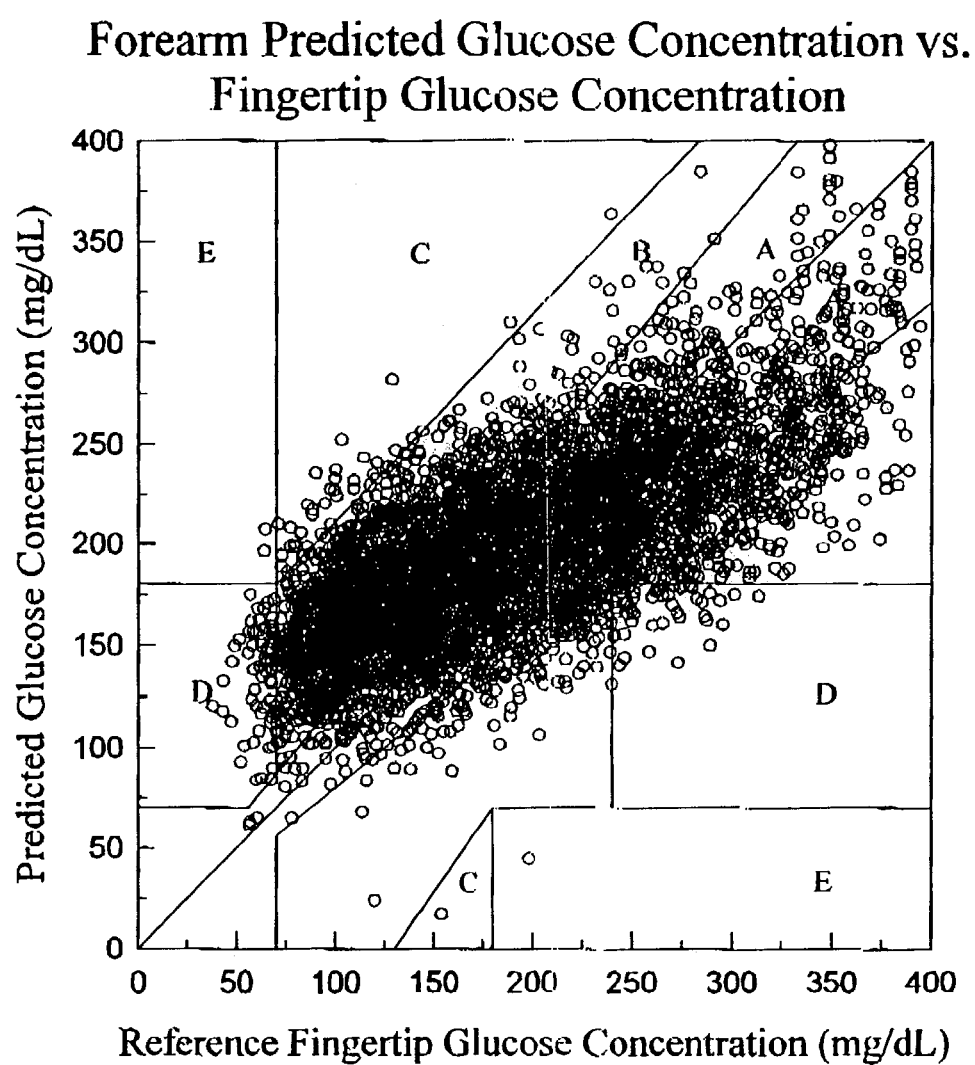
FIG. 9 provides a plot of predicted glucose concentration versus traditional invasive reference glucose concentrations.
Figure 10:
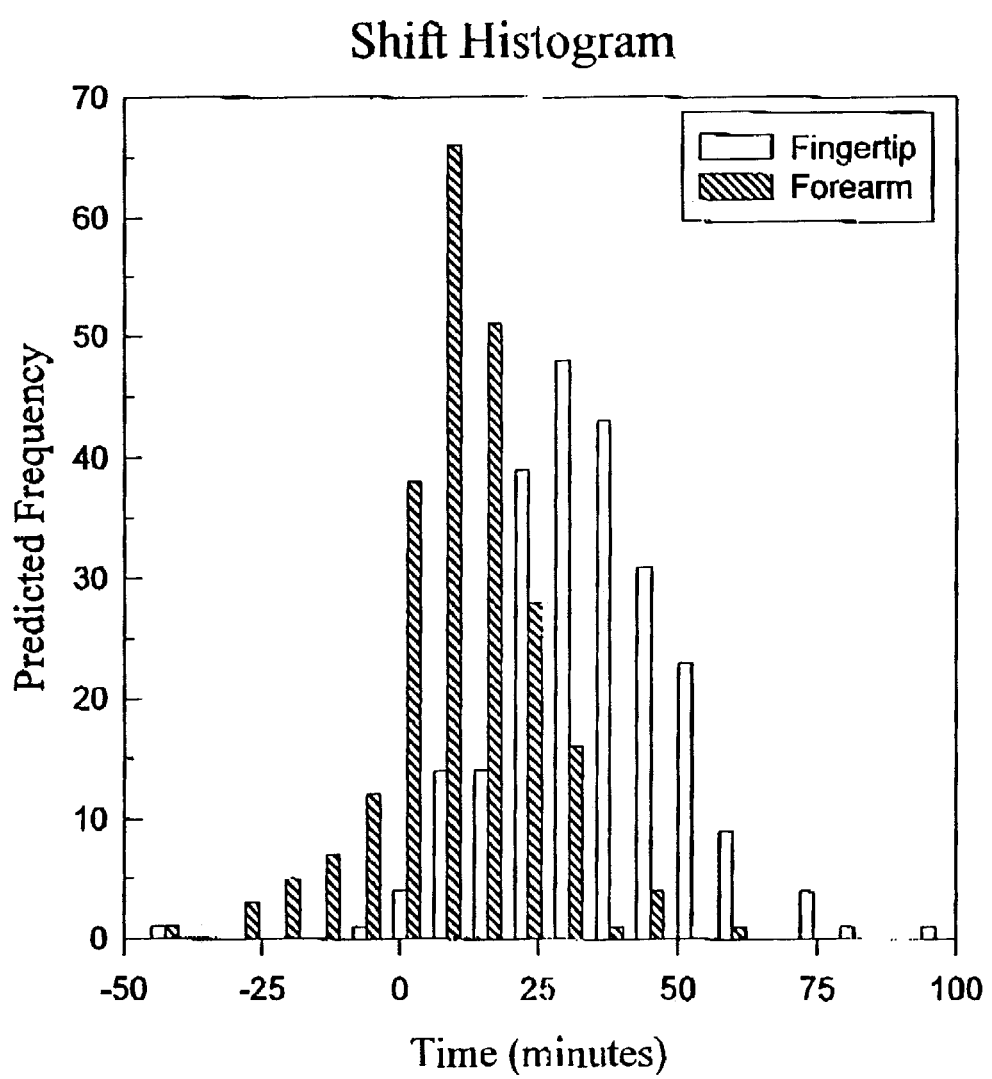
FIG. 10 provides a histogram demonstrating a statistical difference in the histogram shift of predicted glucose concentrations versus fingertip and forearm reference concentrations according to the invention.
Figure 11:
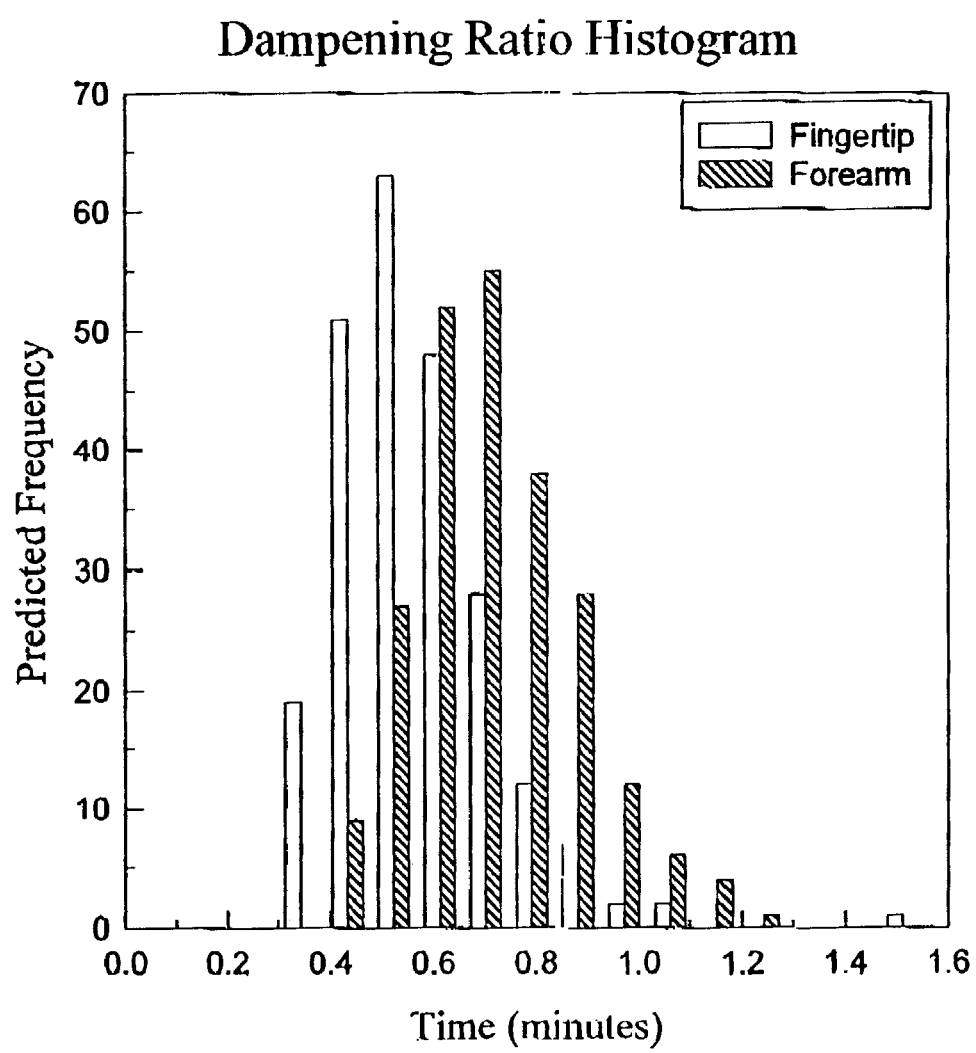
FIG. 11 provides a histogram demonstrating a statistical difference in the histogram magnitude of predicted glucose concentrations versus fingertip and forearm reference concentrations according to the invention.

A concentration correlation plot of the predicted glucose concentrations versus the forearm reference glucose concentrations is presented in FIG. 8. A Clarke error grid analysis for this data demonstrates that 81.9 and 17.9 percent of the data falls into the A and B region, respectively. Thus, 99.8 percent of the data are predicted clinically accurately versus the alternative invasive reference forearm glucose concentrations. However, as shown in FIG. 9, accuracy diminishes when plotted against the corresponding traditional invasive reference fingertip glucose concentrations. Clarke error grid analysis still results in 96.9% of the data in the 'A' or 'B' regions; however, only 51.5% fall into the 'A' region. The correction methodology follows:

- For each subject, lag of the predicted glucose concentration versus reference glucose concentrations for both fingertip and forearm determination is calculated. In order to account for the difference between the predicted values and the reference, a phase correction is calculated using a cross-covariance based algorithm by sliding the x-axis (time vector) of the predicted values a fixed amount to synchronize the predicted and reference values. A histogram of the resultant lags is presented in FIG. 10. Lags for the forearm are observed to range up to sixty-two minutes. The peak of the lag for the comparison against the forearm and the fingertip is approximately ten and 33.6 minutes, respectively. This indicates that the model substantially tracks the forearm glucose concentrations better than glucose concentrations from the fingertip, a result of the model being built with forearm glucose concentrations.
- For each subject, a magnitude correction is calculated comparing the predicted glucose concentrations to each of the fingertip and forearm glucose concentration reference profiles. The magnitude correction constitutes the difference between the glucose concentration ranges of the predicted and reference values. It is observed that the average difference between the predicted and reference glucose concentrations is less for the forearm reference glucose determinations than it is for the fingertip reference glucose determinations. A ratio of the range of the predicted values versus the range of the reference values is calculated for each subject's visit. A histogram of the resulting ratios representative of the magnitude difference is presented in FIG. 11. The histogram demonstrates ratios closer to one for the forearm glucose concentration range with peak values for the forearm and fingertip of 0.71 and 0.55, respectively.
- A third parameter not utilized in this particular model is a correction of the frequency of glucose profile versus time. Thus, the rate of glucose increase to a peak value and the rate of a subsequent decline may differ for traditional invasive glucose determinations and alternative invasive glucose determinations, and this profile shape difference or period may be corrected.

It is here noted that specific examples of parameter calculations are presented, but that those skilled in the art will immediately appreciate that the lag, dampening, and frequency parameters and similar parameters utilized to characterize population differences may be calculated in a number of ways, any of which are consistent with the spirit and scope of the invention. For example, phase correction may be performed with techniques such as a Bessel filter, warping of the time axis and re-sampling, development of a wavelet-based model and subsequent time compression, or shifting. Similarly, magnitude correction may be performed with a simple multiplication factor after centering the data to either the mean or single data point, a multiplication factor dependent upon the rate of change, a multiplication factor dependent upon time, a multiplication factor dependent upon the tissue state, or a multiplication factor dependent upon the type of diabetes or class of tissue. Additionally, it is noted that incomplete vectors may still be utilized to determine these or similar parameters.

A multi-step correction method may then be implemented utilizing one or more of these parameters. In one example, a shift correction is followed by a magnitude correction. First, the mean shift value of 33.6 minutes is subtracted from the prediction time vector. Second, a magnitude correction is performed. Initially, the shift corrected data is mean centered. Then, the resulting glucose concentrations are divided by 0.55. Finally, the mean of the shift corrected data is added to the resulting vector of data.

Figure 12:
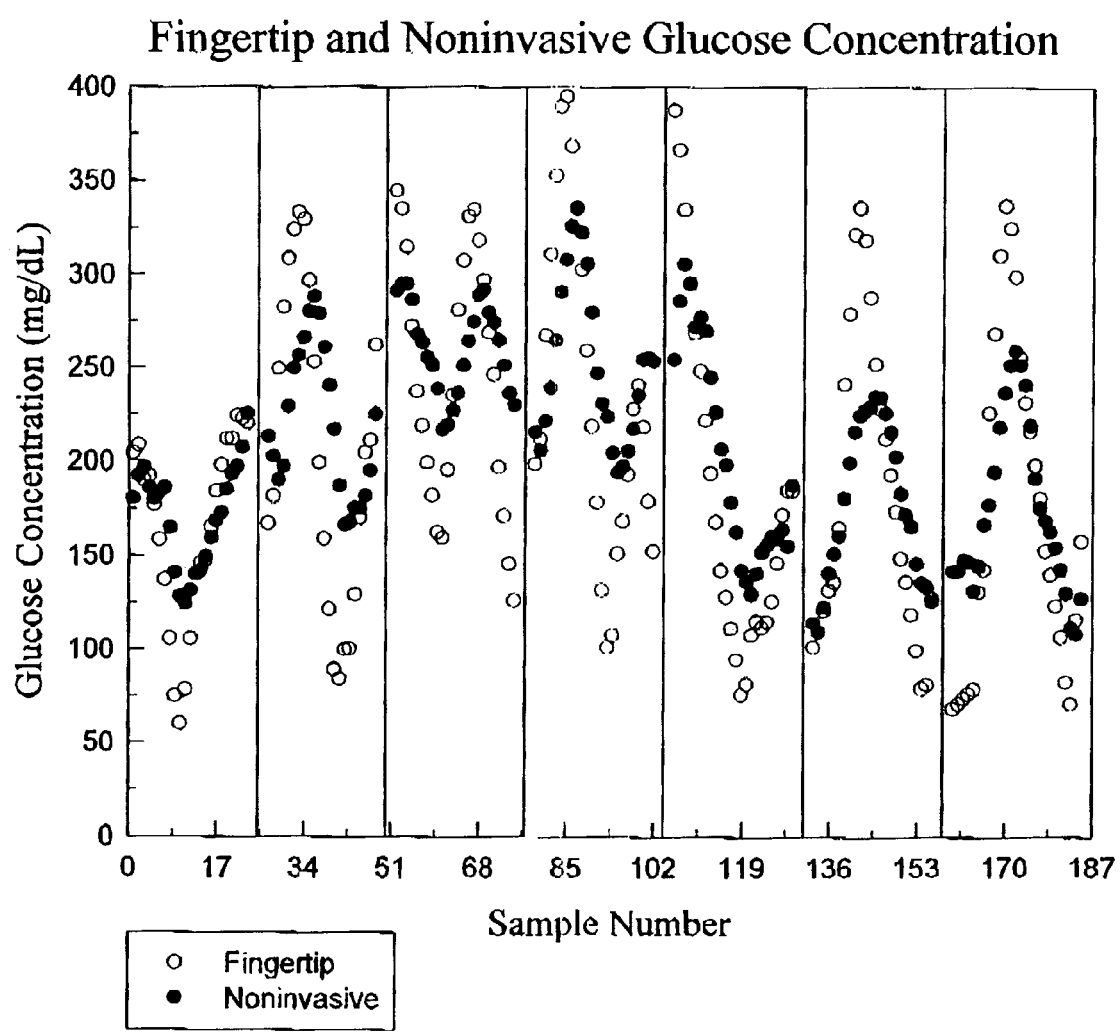
FIG. 12 provides a plot of subjects demonstrating dampened and lagged glucose predictions versus traditional invasive reference glucose concentrations according to the invention.
Figure 13:
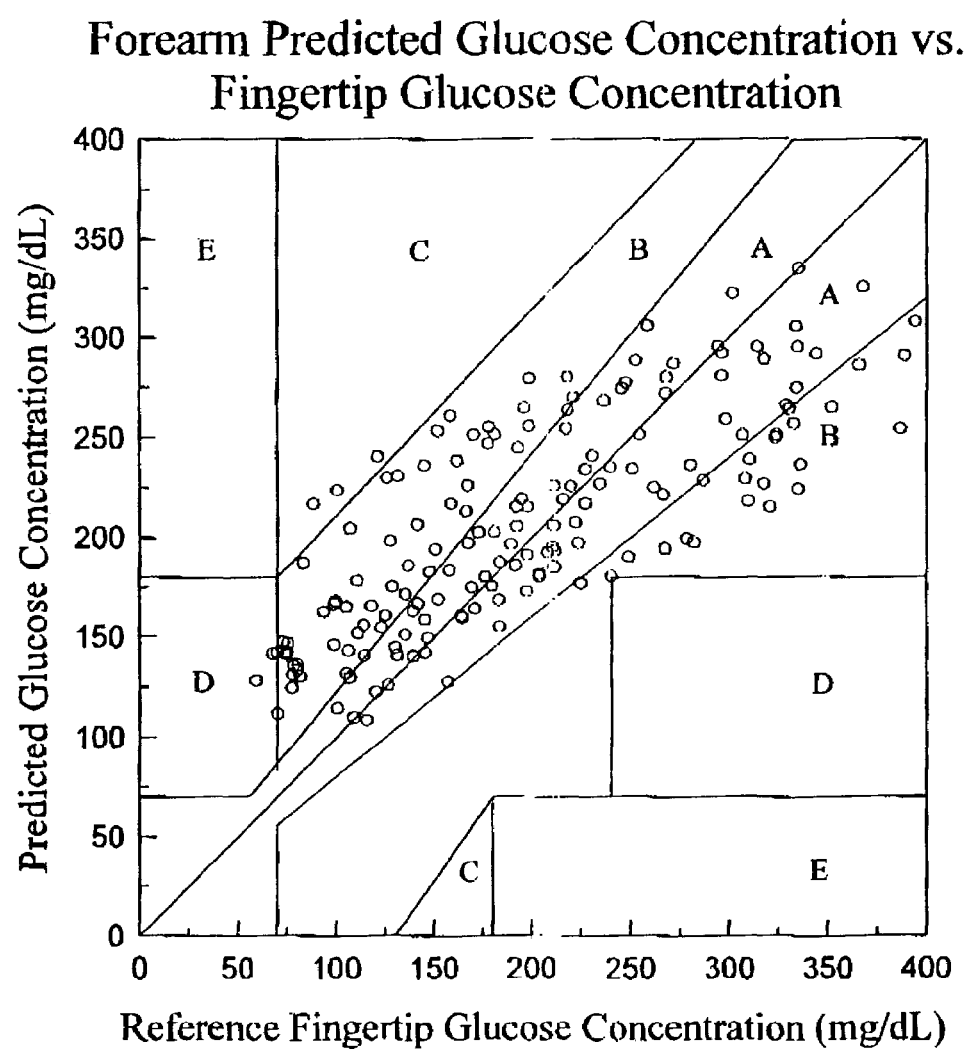
FIG. 13 illustrates a concentration correlation plot of the series of subjects with dampened and lagged glucose predictions versus traditional invasive reference glucose concentrations according to the invention.
Figure 14:
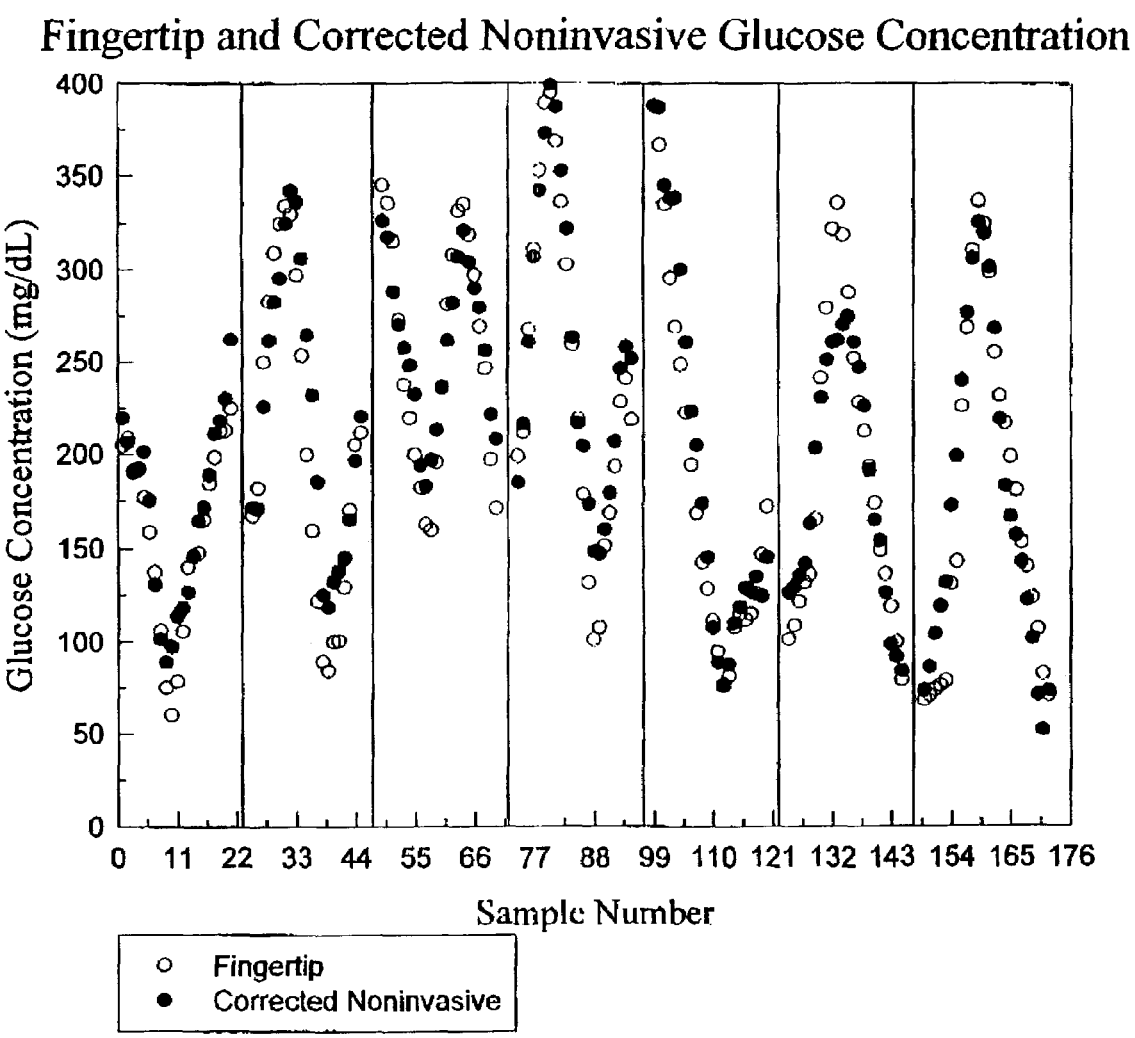
FIG. 14 shows a plot of lag and magnitude adjusted glucose predictions overlaid with traditional invasive glucose determinations according to the invention.
Figure 15:
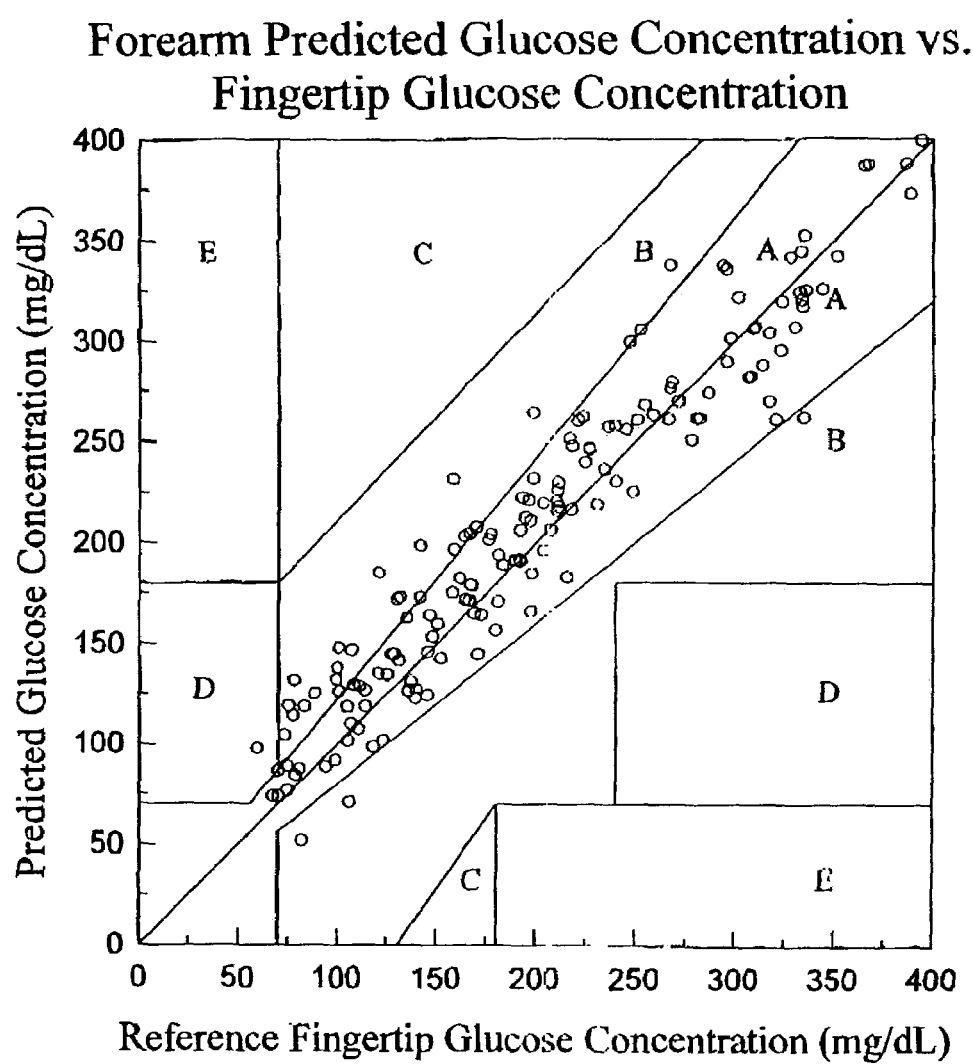
FIG. 15 provides a concentration correlation plot of the lag and magnitude adjusted glucose predictions versus traditional invasive reference glucose concentrations according to the invention.

The two-step correction with parameters of a shift adjustment of 33.6 minutes and a scaling factor of 0.55 produced above is here applied to a set of 7 daily visits from a total of 3 subjects representing noninvasive spectra collected from 3 near-IR glucose analyzers. The fingertip reference glucose concentrations and noninvasively predicted glucose concentration profiles are presented in FIG. 12. The noninvasive glucose concentrations predicted from spectra collected from the forearm are clearly damped and lagged versus the corresponding traditional invasive glucose determinations. The corresponding concentration correlation plot overlaid with a Clarke error grid is presented in FIG. 13. The algorithm corrected glucose profiles and corresponding concentration correlation plot is presented in FIGS. 14 and 15, respectively. Notably, the lag and dampening have been greatly reduced. The respective statistics for the uncorrected and corrected glucose concentrations reveal an obvious improvement in accuracy. The statistics for the uncorrected and corrected glucose concentrations are Clarke 'A' region: 49.7 and 80.5%; r: 0.78 and 0.96, F-value: 2.38 and 10.9, standard error 54.4 and 26.0 mg/dL, respectively.

Figure 16:
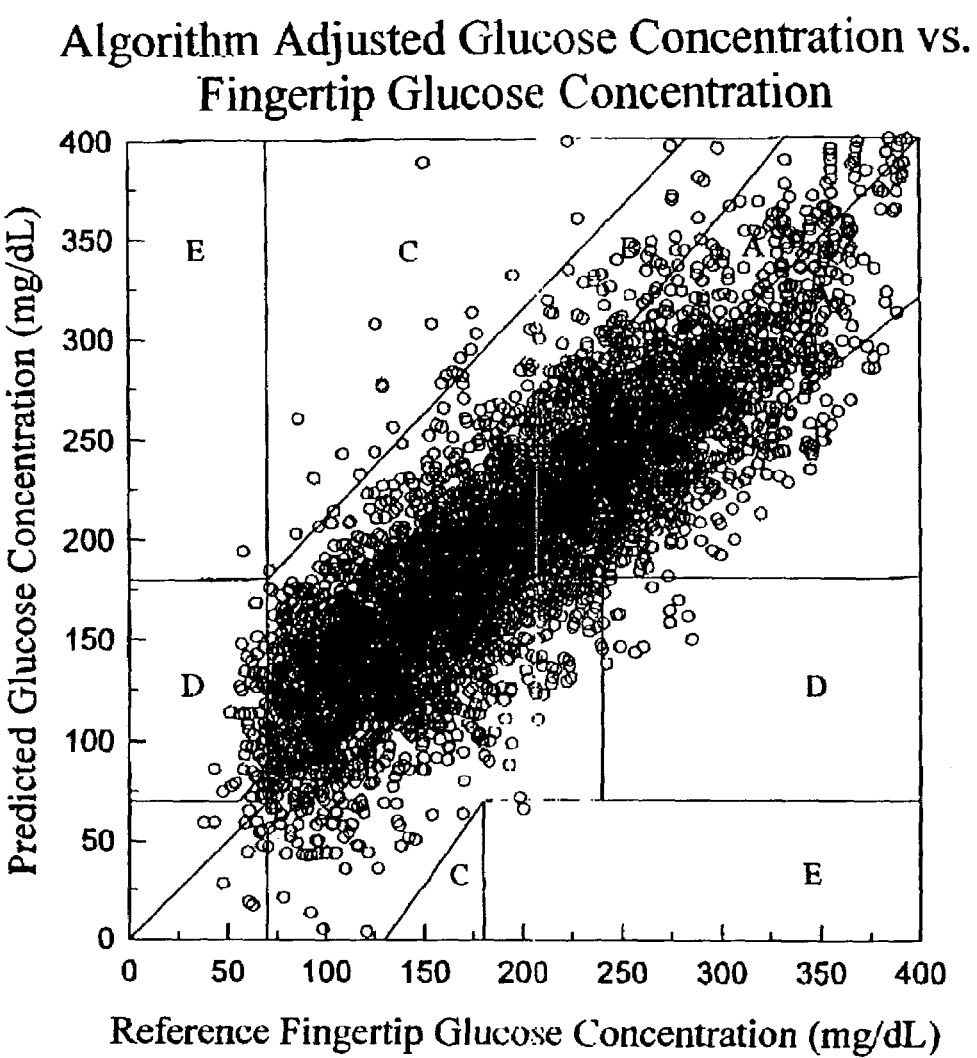
FIG. 16 shows an algorithm-adjusted concentration correlation plot of predicted glucose concentration versus traditional reference glucose concentrations according to the invention.

The two-step correction demonstrated above was applied to the entire data set. The corrected predicted fingertip glucose concentrations are presented in a concentration correlation plot superimposed onto a Clarke error grid, FIG. 16. The corrected glucose concentrations result in 97.8% of the points falling into the 'A' or 'B' region of the Clarke error grid. The correlation coefficient, F-Value, and r value each showed a corresponding increase. In addition, the algorithm allows conversion back and forth between forearm and fingertip glucose concentrations.

While the preceding description has been directed primarily to calibration sets that include invasive reference measurements, embodiments of the invention are possible that employ noninvasive reference measurements. The above data emphasize the importance of taking reference measurements at a site having perfusion equivalence to the sampling site. Accordingly, the principles previously discussed are equally applicable to calibrations developed using noninvasive reference measurements, rather than invasive reference measurements.

Integrated Glucose Analyzer

Figure 17:
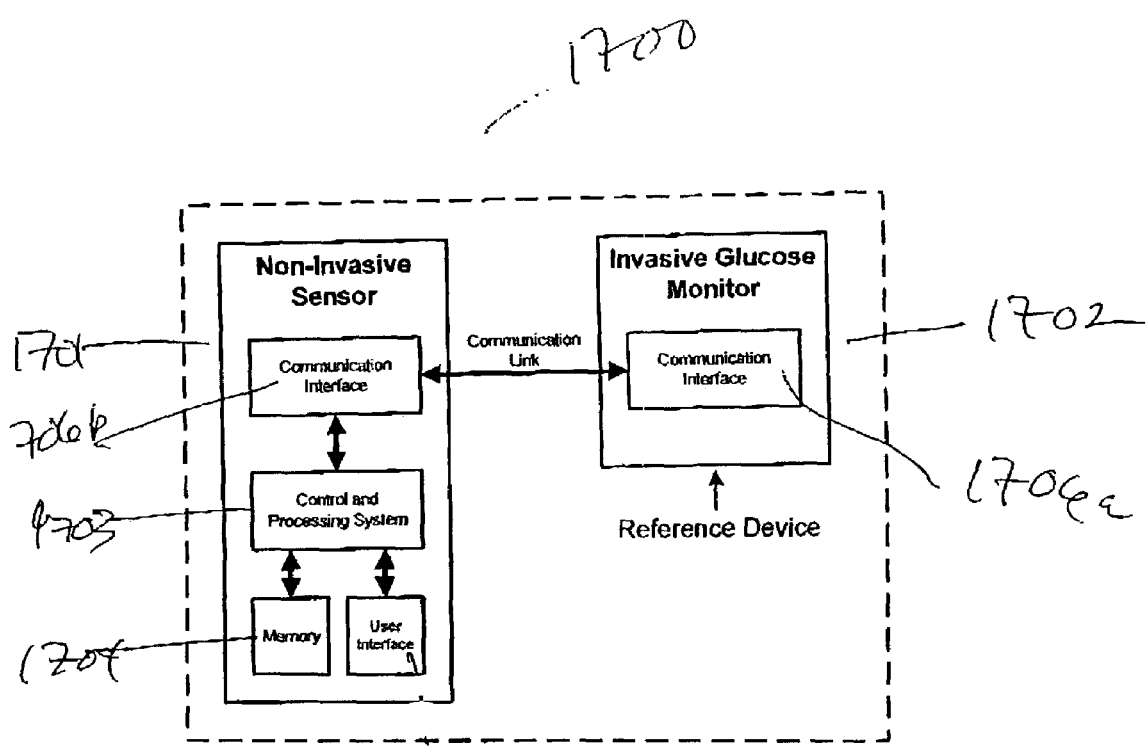
FIG. 17 shows a block diagram of an apparatus including a noninvasive glucose analyzer coupled with an invasive (traditional or alternative) glucose monitor according to the invention.

An integrated glucose analyzer 1700 that utilizes alternative invasive or traditional invasive glucose determinations in combination with noninvasive measurements is shown in FIG. 17.

The invention includes a first component 1701 that measures an analytical signal from the body to determine the body's glucose concentration. Numerous noninvasive devices have been described above. In one embodiment of the invention, a near-infrared spectrometer configured for a noninvasive diffuse reflectance measurement from the forearm may be utilized. The first component 1701 includes a control and processing element 1703 for executing computer-readable instructions and at least one storage element 1704, such as a memory, having executable program code embodied therein for converting a series of reflected near-IR signals, collected from the forearm or other tissue site, into a corresponding series of blood glucose values.

A second component 1702, that provides either a traditional invasive or alternative glucose measurement, is electronically coupled 1706*a* and *b* to the first component. Preferably, the second component provides measurements having five percent error or less.

The above program code also includes code for:
  extracting the data from the traditional second component 1702;
  storing the invasive blood glucose values extracted from the second component 1702 in the storage element 1704 of the first component 1701; and
  using the stored invasive blood glucose values for calibration, calibration assignment, validation, quality assurance procedures, quality control procedures, adjustment, and/or bias correction, depending on the current mode of operation.

For example, in the case of calibration, finger stick-based blood glucose values are collected concurrently with noninvasive spectra to form a calibration set of paired data points. The set is used to calculate a mathematical model suitable for determination of blood glucose on the basis of a noninvasive measurement, such as a spectrum. As a second example, in the case of bias adjustment, invasive blood glucose determinations are collected with the first noninvasive glucose determination of the day and utilized to adjust the noninvasive glucose concentration to the reference glucose determination. The adjustment parameter is utilized until a new invasive reference glucose determination is collected.

The above program code also includes code for:
  providing a comparison and evaluation of the finger stick blood glucose value to the blood glucose value obtained from the noninvasive near-infrared diffuse reflectance measurement.

In one embodiment, information is communicated to the first component 1701 from the second component 1702. Alternatively, the second component 1702 may containing processing and storage elements, instead of the first component. Noninvasive, glucose measurements are configured to operate in modes (transmission, diffuse reflectance, and transflectance) as described above on body parts as described above.

Finally, although the preferred embodiment employs fingerstick measurements, any measurement having sufficient accuracy and precision can be used as the reference measurement.

There is a pronounced disadvantage to conventional systems, in which a primary device and a secondary device are separate and distinct from each other. Secondary measurements must be compared to primary measurements, in order to validate the secondary measurements. Conventionally, comparison requires the consumer to manually input a blood glucose value from the primary device (traditional or alternative invasive glucose analyzer) into the secondary device (noninvasive or implantable glucose analyze) for comparison. An inherent risk to such an approach is the improper input of the primary glucose value into the secondary device, thus resulting in an invalid comparison.

Advantageously, the integrated glucose analyzer eliminates the necessity for the patient to manually input an invasive measurement for comparison with the noninvasive measurement. A second advantage is the ability to utilize a single case for both components with a similar power supply and display. This results in fewer elements that a person with diabetes need carry with them. An additional advantage is a backup glucose analyzer in the event of the noninvasive glucose analyzer failing to produce a glucose value as may be the case with very high or hypoglycemic glucose concentrations. A third advantage is traceability. The time difference between a reference glucose determination from an invasive meter and a corresponding noninvasive glucose reading may be critical in establishing a correction to an algorithm such as a bias. An automated transfer of the glucose value and the associated time greatly reduces risks in usage of a noninvasive analyzer that requires such a correction. Finally, the transfer of glucose and time information into the noninvasive analyzer digital storage means eases subsequent analysis and data management by the individual or a professional.

This technology may be implemented in healthcare facilities including, but not limited to: physician offices, hospitals, clinics, and long-term healthcare facilities. In addition, this technology would be implemented for home-use by consumers who desire to monitor their blood glucose levels whether they suffer from diabetes, impaired glucose tolerance, impaired insulin response, or are healthy individuals.

Additionally, an embodiment is possible in which the first and second components are separate analyzers, the first component configured to measure glucose noninvasively, and the second component configured to perform either alternate invasive or traditional invasive measurements. In the current embodiment, first and second components are electronically coupled by means of a communication interface, such as RS232 or USB (universal serial bus). Other commonly-known methods of interfacing electrical components would also be suitable for the invention, such as telemetry, infrared signals, radiowave, or other wireless technologies. Either embodiment provides the above advantages of eliminating the possibility of invalid measurements by doing away with the necessity of manual data entry.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

What is claimed is:

1. A method of controlling sample site disparity error in calibration of a noninvasive glucose analyzer comprising:
collecting one or more noninvasive signals from a subject's body at an alternative sampling site, said alternative sampling site having a location that is among those sites that are selected when performing an alternative invasive glucose determination, said alternative sampling site being located at a region other than said subject's fingertips or toes;
invasively determining an alternative reference glucose measurement corresponding in time to each noninvasive signal from said body at an alternative reference measurement site, said alternative reference measurement site located at a region of the body having a tissue matrix substantially identical or equivalent to a tissue matrix at said alternative sampling site so that error due to a discrepancy between glucose concentration at said alternative sampling site and said alternative reference measurement site is reduced or eliminated, and;
any of the steps of:
calibrating said glucose analyzer utilizing a calibration model calculated from said one or more noninvasive signals and said alternative reference glucose measurements; and
maintaining calibration of said glucose analyzer by utilizing said one or more noninvasive signals and said alternative reference glucose measurements to select, adjust and/or correct a calibration model.

2. The method of claim 1, wherein said step of invasively determining said alternative reference glucose measurement comprises determining one or more alternative reference glucose measurements utilizing any of:
a lancet;
a laser poration apparatus;
an applied current; and
a suction apparatus.

3. The method of claim 2, wherein said step of determining said one or more alternative reference glucose measurements comprises measuring one or more invasive reference glucose measurements on each of a set of biosamples.

4. The method of claim 3, wherein said set of biosamples comprises any of:
a set of blood samples;
a set of interstitial fluid samples;
a set of interstitial fluid samples selectively sampled from a tissue depth approximately equal to a depth of penetration of an incident signal; and
a set of samples wherein each sample is a mixture of a blood matrix, an interstitial fluid matrix, and a selectively sampled interstitial fluid matrix.

5. The method of claim 1, wherein said noninvasive signals comprise one of:
a reference set of bioimpedance readings;
a reference set of Raman spectra;
a reference set of fluorescence spectra;
a reference set of ultraviolet spectra;
a reference set of visible spectra;
a reference set of near-infrared spectra;
a set of infrared spectra;
a reference set of far-infrared spectra; and
a reference set of mid-infrared spectra.

6. The method of claim 1, wherein said alternative sampling site and said alternative reference measurement site each comprise one of:
a head;
an earlobe;
an eye;
a tongue;
a torso;
an abdominal region;
an arm;
an upper arm;
a forearm;
a volar aspect of a forearm;
a dorsal aspect of a forearm;
a palmar region;
a leg;
a thigh;
a calf; and
a plantar region.

7. The method of claim 1, wherein said alternative sampling site and said alternative reference measurement site each comprise a forearm.

8. The method of claim 1, wherein said alternative reference measurement site is within approximately three inches of said alternative sampling site.

9. The method of claim 1, wherein said alternative reference measurement site is within approximately three inches of a contralateral position of said body compared to said alternative sampling site.

10. The method of claim 1, wherein said step of calibrating comprises any of:
performing a partial least squares analysis;
performing a partial least squares analysis;
performing a principal component regression; and
performing a neural network analysis.

11. The method of claim 1, wherein said one or more noninvasive signals comprise any of:
a series of transmittance measurements;
a series of transflectance measurements; and
a series of diffuse reflectance measurements.

12. The method of claim 11, wherein said one or more noninvasive signals comprise any of:
a set of bioimpedence readings;
a set of Raman spectra;
a set of fluorescence spectra;
a set of ultraviolet spectra;
a set of visible spectra;
a set of near-infrared spectra;
a set of infrared spectra;
a set of far-infrared spectra; and
a set of mid-infrared spectra.

13. The method of claim 12, wherein said set of near-infrared spectra are collected from 1100 to 2500 nm.

14. The method of claim 1, further comprising steps of:
collecting a prediction noninvasive signal; and
predicting a glucose concentration based on said prediction noninvasive signal and said glucose analyzer calibrated using said one or more noninvasive signals and said alternative reference glucose measurements.

15. The method of claim 14, wherein said step of collecting a prediction noninvasive signal is performed on a prediction region of said body comprising one of:
said head;
said earlobe;
said eye;
said tongue;
said torso;
said abdominal region;
said arm;
said upper arm;
said forearm;
said volar aspect of the forearm;

said dorsal aspect of the forearm;
said palmer region;
said leg;
said thigh;
said calf; and
said planter region.

16. The method of claim 15, wherein said step of collecting said prediction noninvasive signal comprises one of:
a transmittance measurement;
a transflectance measurement; and
a diffuse reflectance measurement.

17. The method of claim 16, wherein said prediction noninvasive signal comprises one of:
a bioimpedence reading;
a Raman spectrum;
a fluorescence spectrum;
an ultraviolet spectrum;
a visible spectrum;
a near-infrared spectrum:
a set of infrared spectra;
a set of far-infrared spectra; and
a set of mid-infrared spectra.

18. The method of claim 17, wherein said near-infrared spectrum is collected from 1100 to 2500 nm.

19. The method of claim 16, wherein said prediction region is said forearm.

20. The method of claim 1, wherein said step of maintaining comprises any of:
maintaining a glucose calibration;
adjusting a calibration;
performing a bias correction;
generating a calibration assignment;
performing a validation;
performing a quality assurance procedure; and
performing a quality control procedure.

21. A method of controlling sample site disparity error in calibration of an implantable glucose analyzer, comprising the steps of:
collecting one or more signals at a first site from a subject's body using said implantable glucose analyzer, said first site being located at a region other than said subject's fingertips or toes;
determining an alternative reference glucose measurement corresponding in time to each of said one or more signals from said body at an alternative reference measurement site, said alternative reference measurement site located at a region of the body having a tissue matrix substantially identical or equivalent to a tissue matrix at said first site so that error due to a discrepancy between glucose concentration at said first site and said alternative reference measurement site is reduced or eliminated, and:
any of the steps of:
calibrating said glucose analyzer utilizing a calibration model calculated from said one or more signals and said alternative reference glucose measurements; and
maintaining calibration of said glucose analyzer by utilizing said one or more signals and reference glucose measurements to select, adjust and/or correct a calibration model.

22. The method of claim 21, wherein said step of determining said alternative reference glucose measurement comprises determining an invasive reference glucose measurement utilizing any of:
a lancet;
a laser poration apparatus;
an applied current; and
a suction apparatus.

23. The method of claim 22, wherein said step of determining said invasive reference glucose measurements comprises measuring one or more invasive reference glucose measurements on each of a set of biosamples.

24. The method of claim 23, wherein said set of biosamples comprises any of:
a set of blood samples;
a set of interstitial fluid samples;
a set of interstitial fluid samples selectively sampled from a tissue depth approximately equal to a depth of penetration of an incident signal;
a set of samples wherein each sample is a mixture of a blood matrix, an interstitial fluid matrix, and a selectively sampled interstitial fluid matrix.

25. The method of claim 21, wherein said alternative reference glucose measurements comprises any of:
a reference set of bioimpedence readings;
a reference set of Raman spectra;
a reference set of fluorescence spectra;
a reference set of ultraviolet spectra;
a reference set of visible spectra;
a reference set of near-infrared spectra;
a set of infrared spectra;
a set of far-infrared spectra; and
a set of mid-infrared spectra.

26. The method of claim 21, wherein said first site comprises a peritoneal cavity.

27. The method of claim 26, wherein said alternative reference measurement site is located on any of:
a head;
an earlobe;
an eye;
a tongue;
a torso;
an abdominal region;
an arm;
an upper arm;
a forearm;
a volar aspect of a forearm;
a dorsal aspect of a forearm;
a palmar region;
a leg;
a thigh;
a calf; and
a plantar region.

28. The method of claim 21, wherein said step of calibrating further comprises any of the steps of:
performing a partial least squares analysis;
performing a principal component regression analysis; and
performing a neural network analysis.

29. The method of claim 21, wherein said one or more signals comprise any of:
a series of transmittance measurements;
a series of transflectance measurements; and
a series of diffuse reflectance measurements.

30. The method of claim 29, wherein said one or more signals comprise any of:
a set of bioimpedence readings;
a set of Raman spectra;
a set of fluorescence spectra;
a set of ultraviolet spectra;
a set of visible spectra;
a set of near-infrared spectra;
a set of infrared spectra;

a set of far-infrared spectra; and a set of mid-infrared spectra.

31. The method of claim 30, wherein said set of near-infrared spectra are collected from 1100 to 2500 nm.

32. The method of claim 21, further comprising steps of:

collecting a prediction signal; and predicting a glucose concentration based on said prediction signal and said glucose analyzer calibrated using said one or more signals and said alternative reference glucose measurements.

33. The method of claim 32, wherein said step of collecting a prediction signal is performed on a prediction region of said body comprising a peritoneal cavity.

34. The method of claim 33, wherein said step of collecting said prediction signal comprises one of:

a transmittance measurement;

a transflectance measurement; and a diffuse reflectance measurement.

35. The method of claim 34, wherein said prediction signal comprises one of:

a bioimpedence reading;

a Raman spectrum;

a fluorescence spectrum;

an ultraviolet spectrum;

a visible spectrum;

a near-infrared spectrum;

a set of infrared spectra;

a set of far-infrared spectra; and a set of mid-infrared spectra.

36. The method of claim 35, wherein said near-infrared spectrum is collected from 1100 to 2500 nm.

37. The method of claim 21, wherein said step of maintaining comprises any of:

maintaining a glucose calibration;

adjusting a calibration;

performing a bias correction;

generating a calibration assignment;

performing a validation;

performing a quality assurance procedure; and performing a quality control procedure.

* * * * *